(12) United States Patent
Park et al.

(10) Patent No.: US 9,914,082 B2
(45) Date of Patent: Mar. 13, 2018

(54) AIR CLEANER

(71) Applicant: LG ELECTRONICS INC., Seoul (KR)

(72) Inventors: Jaekyun Park, Seoul (KR); Hyunpil Ha, Seoul (KR); Soonki Jung, Seoul (KR); Yeongcheol Mun, Seoul (KR); Soohyun Bae, Seoul (KR); Sangjun Yoon, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 0 days.

(21) Appl. No.: 15/364,369

(22) Filed: Nov. 30, 2016

(65) Prior Publication Data
US 2017/0246570 A1 Aug. 31, 2017

(30) Foreign Application Priority Data

Feb. 26, 2016 (KR) .................... 10-2016-0023663
Oct. 13, 2016 (KR) .................... 10-2016-0132790
Oct. 25, 2016 (KR) .................... 10-2016-0139376

(51) Int. Cl.
B01D 46/00 (2006.01)
B01D 46/24 (2006.01)
(Continued)

(52) U.S. Cl.
CPC ..... *B01D 46/0005* (2013.01); *B01D 46/0041* (2013.01); *B01D 46/0047* (2013.01);
(Continued)

(58) Field of Classification Search
CPC combination set(s) only.
See application file for complete search history.

(56) References Cited

U.S. PATENT DOCUMENTS 4,365,980 A    12/1982  Culbert et al.
5,117,652 A *  6/1992   Takeuchi ............... F24F 1/025
                                                      62/291
(Continued)

FOREIGN PATENT DOCUMENTS

CN    102661295     12/2014
CN    204141826     2/2015
(Continued)

OTHER PUBLICATIONS

Machine translation of KR 10-1168738, with a publication date of Jul. 26, 2012.*

(Continued)

*Primary Examiner* — Robert Clemente
(74) *Attorney, Agent, or Firm* — Ked & Associates LLP

(57) ABSTRACT

An air cleaner is provided that may include a cylindrical case including an inlet through which air is suctioned in a radial direction into the cylindrical case; a filter configured to be detachably provided in the case and having a cylindrical shape; and a filter frame configured to support the filter. The filter frame may include a lower frame provided at a lower portion of the filter; an upper frame provided at an upper portion of the filter; and a plurality of supporting frames that extends toward the upper frame from the lower frame. An entry portion for the suctioned air may be formed between the plurality of support frames, the entry portion being configured to receive the filter.

20 Claims, 19 Drawing Sheets

(51) Int. Cl.
*B01D 46/42* (2006.01)
*F24F 1/02* (2011.01)
*F24F 1/00* (2011.01)

(52) U.S. Cl.
CPC .......... *B01D 46/24* (2013.01); *B01D 46/2411* (2013.01); *B01D 46/4227* (2013.01); *F24F 1/02* (2013.01); *F24F 2001/004* (2013.01)

(56) References Cited

U.S. PATENT DOCUMENTS

| | | | |
|---|---|---|---|
| 5,264,015 | A | 11/1993 | Matsui |
| 5,334,248 | A | 8/1994 | Kwak |
| 5,641,343 | A | 6/1997 | Frey |
| 5,753,000 | A | 5/1998 | Chiu et al. |
| 6,494,940 | B1 * | 12/2002 | Hak .......................... A61L 9/16 55/471 |
| 8,212,146 | B1 | 7/2012 | Moore |
| 2006/0107834 | A1 | 5/2006 | Vandenbelt et al. |
| 2006/0201119 | A1 | 9/2006 | Song |
| 2006/0277875 | A1 | 12/2006 | Schuld |
| 2007/0137489 | A1 | 6/2007 | Luo |
| 2007/0221061 | A1 * | 9/2007 | Steiner ...................... B03C 3/32 96/63 |
| 2010/0225012 | A1 * | 9/2010 | Fitton ....................... F24F 1/01 261/116 |
| 2011/0308210 | A1 * | 12/2011 | Crabtree ............ B01D 46/0005 55/483 |
| 2013/0055692 | A1 | 3/2013 | Cecchi et al. |
| 2014/0216259 | A1 | 8/2014 | Iwaki |
| 2015/0306533 | A1 * | 10/2015 | Matlin ................. B01D 46/448 96/420 |
| 2016/0184753 | A1 * | 6/2016 | Chu .................... B01D 46/002 96/74 |

FOREIGN PATENT DOCUMENTS

| | | |
|---|---|---|
| CN | 104406235 | 3/2015 |
| CN | 104603545 | 5/2015 |
| DE | 9312051 | 10/1993 |
| EP | 1 950 500 | 7/2008 |
| EP | 2 072 920 | 6/2009 |
| EP | 2 476 968 | 7/2012 |
| EP | 2 837 897 | 2/2015 |
| EP | 2 853 835 | 4/2015 |
| GB | 2 345 005 | 6/2000 |
| GB | 2516058 | 1/2015 |
| JP | H 06-50180 | 6/1994 |
| JP | 2000-354724 | 12/2000 |
| JP | 2006-022977 | 1/2006 |
| JP | 2007-105578 | 4/2007 |
| JP | 2012-120720 | 6/2012 |
| JP | 2013-217580 | 10/2013 |
| JP | 2014-507277 | 3/2014 |
| JP | 2014-119224 | 6/2014 |
| JP | 2015-080737 | 4/2015 |
| JP | 2015-108497 | 6/2015 |
| JP | 5740503 | 6/2015 |
| KR | 20-1993-0002444 | 5/1993 |
| KR | 10-0139487 | 6/1998 |
| KR | 20-0173274 | 3/2000 |
| KR | 20-0289687 | 9/2002 |
| KR | 20-0342073 | 2/2004 |
| KR | 10-2004-0056151 | 6/2004 |
| KR | 10-2004-0108462 | 12/2004 |
| KR | 10-0508312 | 8/2005 |
| KR | 10-2006-0023457 | 3/2006 |
| KR | 10-2009-0058446 | 6/2009 |
| KR | 10-2010-0056797 | 5/2010 |
| KR | 10-2005-0115343 | 6/2010 |
| KR | 10-2010-0062121 | 6/2010 |
| KR | 10-2010-0070069 | 6/2010 |
| KR | 10-2012-0060279 | 6/2012 |
| KR | 10-2012-0071992 | 7/2012 |
| KR | 10-1168738 | 7/2012 |
| KR | 10-2012-0136137 | 12/2012 |
| KR | 10-2013-0036447 | 4/2013 |
| KR | 10-1342606 | 12/2013 |
| KR | 10-2014-0039703 | 4/2014 |
| KR | 10-1385290 | 4/2014 |
| KR | 10-2014-0092953 | 7/2014 |
| KR | 10-2014-0094414 | 7/2014 |
| KR | 10-2014-0096971 | 8/2014 |
| KR | 10-2015-0005594 | 1/2015 |
| KR | 10-1500501 | 3/2015 |
| KR | 10-1512664 | 4/2015 |
| KR | 10-1516365 | 5/2015 |
| KR | 10-2016-0012796 | 2/2016 |
| KR | 10-2016-0015084 | 2/2016 |
| KR | 10-2016-0017587 | 2/2016 |
| KR | 10-1599634 | 3/2016 |
| KR | 10-2016-0048499 | 5/2016 |
| KR | 10-2016-0053649 | 5/2016 |
| WO | WO 2010/109944 | 9/2010 |
| WO | WO 2015/171571 | 11/2015 |

OTHER PUBLICATIONS

United States Office Action dated Jan. 20, 2017 issued in U.S. Appl. No. 15/363,156.
United States Office Action dated Jan. 23, 2017 issued in U.S. Appl. No. 15/363,204.
United States Office Action dated Jan. 23, 2017 issued in U.S. Appl. No. 15/364,410.
United States Office Action dated Jan. 23, 2017 issued in U.S. Appl. No. 15/364,467.
United States Office Action dated Feb. 10, 2017 issued in co-pending U.S. Appl. No. 15/363,111.
Korean Office Action dated Jan. 26, 2017 issued in Application No. 10-2016-0073055.
Korean Office Action dated Jan. 26, 2017 issued in Application No. 10-2016-0073083.
Korean Office Action dated Jan. 26, 2017 issued in Application No. 10-2016-0077888.
International Search Report dated Mar. 21, 2017 issued in Application No. PCT/KR2016/013907.
International Search Report dated Mar. 20, 2017 issued in Application No. PCT/KR2016/013906.
International Search Report dated Mar. 30, 2017 issued in Application No. PCT/2016/013912.
International Search Report dated Mar. 30, 2017 issued in Application No. PCT/KR2016/013908.
Korean Office Action dated Apr. 20, 2017 issued in Application No. 10-2016-0132790.
European Search Report dated Jun. 21, 2017 issued in Application No. 16201095.3.
European Search Report dated Apr. 25, 2017 issued in Application No. 16201086.2-1602.
European Search Report dated Apr. 25, 2017 issued in Application No. 17157045.0-1602.
Korean Office Action dated Jun. 21, 2017 (10-2017-0056865).
Korean Office Action dated Jun. 21, 2017 (10-2017-0056885).
Korean Office Action dated Jun. 21, 2017 (10-2017-0056886).
European Search Report dated Jul. 20,2017 issued in Application No. 16201090.4.
Korean Office Action dated Aug. 31, 2017 issued in Application No. 10-2016-0073090.
U.S. Appl. No. 15/363,111, filed Nov. 29, 2016.
U.S. Appl. No. 15/363,156, filed Nov. 29, 2016.
U.S. Appl. No. 15/659,869, filed Jul. 26, 2017.
U.S. Appl. No. 15/659,878, filed Jul. 26, 2017.
U.S. Appl. No. 15/363,204, filed Nov. 29, 2016.
U.S. Appl. No. 15/364,467, filed Nov. 30, 2016.
U.S. Appl. No. 15/660,105, filed Jul. 26, 2017.
U.S. Appl. No. 15/660,122, filed Jul. 26, 2017.
U.S. Appl. No. 15/363,438, filed Nov. 29, 2016.
U.S. Appl. No. 15/363,587, filed Nov. 29, 2016.
U.S. Appl. No. 15/659,989, filed Jul. 26, 2017.

(56) References Cited

OTHER PUBLICATIONS

U.S. Appl. No. 15/660,076, filed Jul. 26, 2017.
U.S. Appl. No. 15/660,207, filed Jul. 26, 2017.
U.S. Appl. No. 15/660,287, filed Jul. 26, 2017.
U.S. Appl. No. 15/660,362, filed Jul. 26, 2017.
U.S. Appl. No. 15/660,462, filed Jul. 26, 2017.
U.S. Appl. No. 15/363,643, filed Nov. 29, 2016.
U.S. Appl. No. 15/364,410, filed Nov. 30, 2016.
U.S. Appl. No. 15/441,957, filed Feb. 24, 2017.
European Search Report dated Jul. 14, 2017 issued in Application No. 16201092.0.
Korean Office Action dated Aug. 31, 2017 issued in Application No. 10-2016-0073063.
European Search Report dated Jun. 21, 2017 issued in Application No. 16201093.8.
Korean Office Action dated Jun. 21, 2017 issued in Application No. 10-2017-0056789.
Korean Office Action dated Jun. 21, 2017 issued in Application No. 10-2017-0056790.
Korean Office Action dated Jun. 21, 2017 issued in Application No. 10-2017-0056791.
European Search Report dated Jun. 23, 2017 issued in Application No. 16201089.6.
European Search Report dated Jun. 23, 2017 issued in Application No. 16201088.8.
Korean Office Action dated Jun. 30, 2017 issued in Application No. 10-2017-0056864.
European Search Report dated Jul. 14, 2017 issued in Application No. 16201094.6.
European Search Report dated Jul. 20, 2017 issued in Application No. 16201091.2.
Korean Notice of Allowance dated Aug. 15, 2017 issued in Application No. 10-2016-0074369.
Korean Office Action dated Aug. 22, 2017 issued in Application No. 10-2016-0073055.
U.S. Appl. No. 15/364,369, filed Nov. 30, 2016.
Korean Office Action dated Oct. 31, 2017.

\* cited by examiner

AIR CLEANER

CROSS-REFERENCE TO RELATED APPLICATION(S)

The present application claims priority under 35 U.S.C. 119 and 35 U.S.C. 365 to Korean Patent Application No. 10-2016-0132790 filed in Korea on Oct. 13, 2016, No. 10-2016-0023663 filed in Korea on Feb. 26, 2016, and No. 10-2016-0139376 filed in Korea on Oct. 25, 2016, which are hereby incorporated by reference in their entirety.

BACKGROUND

1. Field

An air cleaner is disclosed herein.

2. Background

An air cleaner is a device that suctions in and purifies contaminated air and then discharges purified air. For example, the air cleaner may include a blower that introduces outside air into the air cleaner and a filter capable of filtering dust and bacteria, for example.

Generally, the air cleaner is configured to purify an indoor space, such as a home or an office. According to the air cleaner in the related art, there is a problem that a capacity thereof is limited, and thus, purification of air in an entire indoor space is limited. Accordingly, air around the air cleaner is purified whereas air in a space away from the air cleaner is not purified.

In order to solve this problem, there are efforts to improve a performance of a fan provided in the air cleaner. However, noise generated by the fan gradually increases as a blowing amount of the fan increases. Accordingly, there is a problem is that reliability of the product is decreased. Finally, there is inconvenience that the air cleaner has to be moved by a user in order to purify air in the desired space.

A related art air cleaner is disclosed in Korean Publication No. KR10-2012-0071992 published on Jul. 3, 2012 and entitled AIR CLEANER, which is hereby incorporated by reference. According to this disclosure, air cleaning components, such as the fan and a filter are installed, in an inside of a case having a substantially rectangular parallelepiped shape of a main body of the air cleaner. Air suction ports are formed on a side portion and a lower portion of the main body of the air cleaner and an air discharge port is formed on an upper portion of the main body thereof.

According to this configuration, there is a problem in that a suction capacity is reduced as the contaminated air is suctioned from a limited direction, that is, from a side direction and a lower direction relative to the air cleaner. A corner portion of the case having a rectangular parallelepiped shape provides structural resistance interfering with the suction of air.

In addition, there is a problem that an air cleaning function is limited as purified air does not flow to a space away from the air cleaner, whereas air around the air cleaner is purified. That is, the air which is purified in the air cleaner is discharged in only one direction, that is, only in an upward direction. Further, there is a problem that a blowing capacity is limited as only one blowing fan is provided in the main body of the air cleaner.

BRIEF DESCRIPTION OF THE DRAWINGS

Embodiments will be described in detail with reference to the following drawings in which like reference numerals refer to like elements, and wherein.

DETAILED DESCRIPTION

Figure 1:
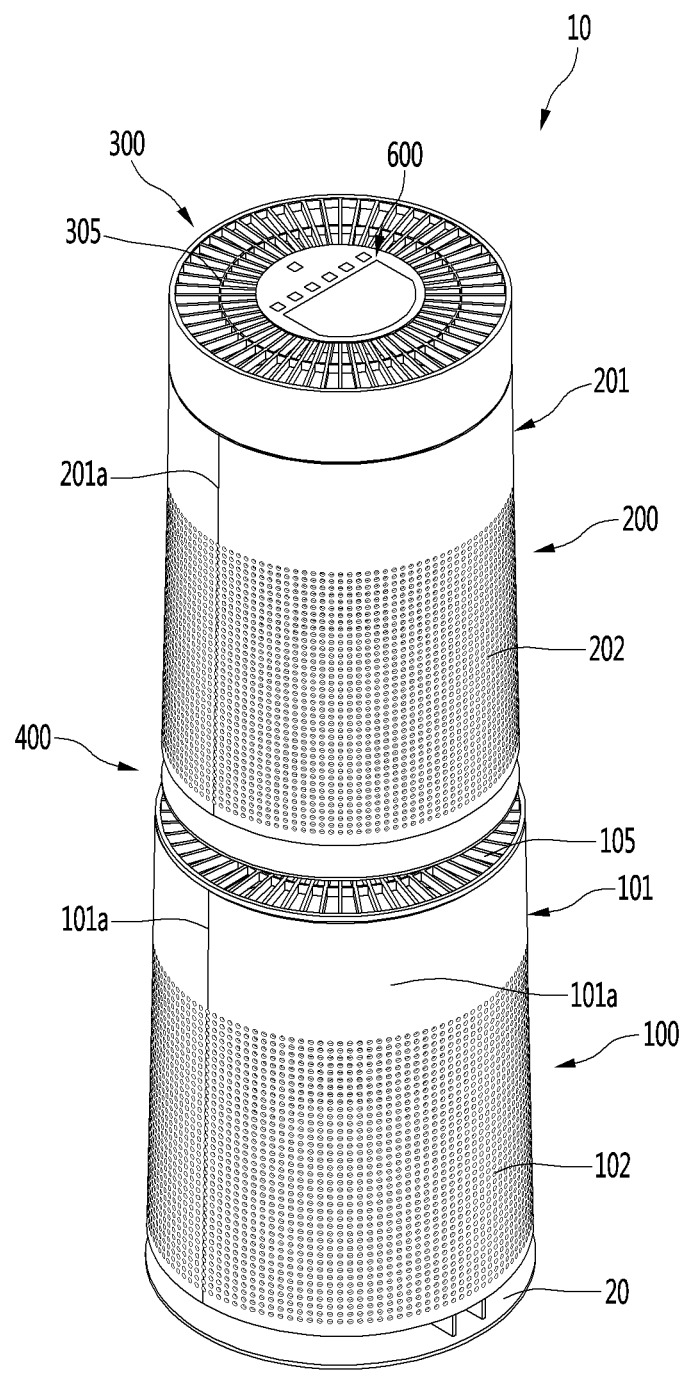
FIG. 1 is a perspective view of an air cleaner according to an embodiment.

Hereinafter, embodiments will be described in detail with reference to the illustrative drawings. Regarding the reference numerals assigned to the components in the drawings, it should be noted that the same components may be designated by the same reference numerals, wherever possible, even though they are shown in different drawings. Also, in the description of embodiments, specific description of known related configuration or functions may be omitted when it is deemed that such description may cause ambiguous interpretation of the present invention.

Also, in the description of embodiments, terms such as first, second, A, B, (a), (b) or the like may be used herein when describing components. Each of these terminologies is not used to define an essence, order or sequence of a corresponding component but used merely to distinguish the corresponding component from other component(s). In a case where it is described that any component is "connected" or "coupled" to another component, the component may be directly or indirectly connected or coupled to another component. However, it is to be understood that another component may be "connected" or "coupled" between the components.

Also, in the description of embodiments, terms such as first, second, A, B, (a), (b) or the like may be used herein when describing components. Each of these terminologies is not used to define an essence, order or sequence of a corresponding component but used merely to distinguish the corresponding component from other component(s). In a case where it is described that any component is "connected" or "coupled" to another component, the component may be directly or indirectly connected or coupled to another component. However, it is to be understood that another component may be "connected" or "coupled" between the components.

FIG. 1 is a perspective view of an air cleaner according to an embodiment. With reference to FIG. 1, the air cleaner 10 according to this embodiment may include blowing devices or blowers 100 and 200 that generate air flow and a flow adjusting device or adjuster 300 that adjusts a discharge direction of the air flow generated in the blowing devices 100 and 200. The blowing devices 100 and 200 may include a first blowing device 100 that generates a first air flow and a second blowing device 200 that generates a second air flow.

The first blowing device 100 and the second blowing device 200 may be provided in a vertical direction. For example, the second blowing device 200 may be provided on or at an upper side of the first blowing device 100. In this case, the first air flow is a flow of indoor air suctioned from a lower side of the air cleaner 10 and the second air flow is a flow of indoor air suctioned from an upper side of the air cleaner 10.

The air cleaner 10 may include cases 101 and 201 that form an outer appearance thereof. That is, the cases 101 and 201 may include a first case 101 that forms an outer appearance of the first blowing device 100. The first case 101 may have a cylindrical shape. An upper portion of the first case 101 may have a diameter which is less than a diameter of a lower portion thereof. That is, the first case 101 may have a truncated cone shape.

The first blowing device 100 and the second blowing device 200 may be referred to as a "first air cleaning module or cleaner 100" and a "second air cleaning module or cleaner 200", respectively, in that the first blowing device 100 and the second blowing device 200 perform a function of cleaning air in a space to be cleaned. The first blowing device 100 may be referred to as a "lower air cleaning module or cleaner" or "lower module or cleaner" in that the first blowing device 100 is provided at a lower portion of the air cleaner 10 and the second blowing device 200 may be referred to as an "upper air cleaning module or cleaner" or "upper module or cleaner" in that the second blowing device 200 is provided at an upper portion of the air cleaner 10. The flow adjusting device 300 may be referred to as "flow adjusting module or adjuster 300" or "flow control module 300".

The first case 101 may include a first separation portion 101a which assembles or disassembles two parts which form the first case 101. If at least one of the two parts is separated, the first case 101 may be opened. Inner components of the first blowing device 100 may be replaced or repaired by opening the first case 101.

The first case 101 may include a first suction portion or inlet 102 through which air may be suctioned in a radial direction. The first suction portion 102 may include one or more through hole formed to pass through at least a portion of the first case 101. A plurality of first suction portions 102 may be provided.

The plurality of first suction portions 102 may be evenly provided in a circumferential direction along an outer circumferential surface of the first case 101 so that air suction may be performed in any direction relative to the first case 101. That is, air may be suctioned in 360 degree directions relative to a center line that extends in the vertical direction and passes through an inside center of the first case 101.

Accordingly, a suction amount of air may be increased by the first case 101 having a cylindrical shape and the plurality of first suction portions 102 formed along the outer circumferential surface of the first case 101. Flow resistance to suctioned air may be reduced by avoiding a cube shape having edges or edge portions such as the case of the related art air cleaner.

Air which is suctioned in through the first suction portion 102 may flow substantially in the radial direction from the outer circumferential surface of the first case 101. Directions may be defined as follows. Referring to the FIG. 1, the vertical direction may refer to an axial direction and a transverse direction may refer to the radial direction. The axial direction may correspond to a central axis direction of the first fan 160 and the second fan 260, which are described hereinafter, that is, a motor shaft direction of the fan. The radial direction may refer to a direction which is perpendicular to the axial direction. The circumferential direction may refer to a virtual circle direction which is formed when rotating about the axial direction and having a distance of the radial direction as a rotational radius.

The first blowing device 100 may include a base 20 provided at a lower side of the first case 101 and placed on the ground. The base 20 may be positioned spaced apart from a lower end portion or end of the first case 101 in a downward direction. A base suction portion or inlet 103 may be formed in a space between the first case 101 and the base 20.

Air which is suctioned in through the base suction portion 103 may flow in an upward direction through a suction port 112 of a suction grill 110 (see FIG. 2), which may be provided in or at an upper side of the base 20. That is, the first blowing device 100 may include the plurality of suction portions 102 and the base suction portion 103. Air in a lower portion of the indoor space may be easily introduced to the first blowing device 100 through the plurality of suction portions 102 and the base suction portion 103. Accordingly, the suction amount of air may be increased.

A first discharge portion or outlet 105 may be formed at an upper portion of the first blowing device 100. The first discharge portion 105 may be formed on a first discharge grill 195 of a first discharge guide device or guide 190 (see, FIG. 8) which may be provided in the first blowing device 100. The first discharge guide 190 may form an outer appearance of an upper end portion or end of the first blowing device 100. Air discharged through the first discharge portion 105 may flow to the upper side in the axial direction.

A second case 201 may include a second separation portion 201a which assembles or disassembles two parts which form the second case 201. If at least one of the two parts is separated, the second case 201 may be opened. Inner components of the second blowing device 200 may be replaced or repaired by opening the second case 201.

A diameter of a lower end portion of the second case 201 may be less than a diameter of the upper end portion or end of the first case 101. Accordingly, in a general shape of the cases 101 and 201, a lower cross-sectional area of the cases 101 and 102 may be formed to be greater than an upper cross-sectional area. Accordingly, the air cleaner 10 may be stably supported on the ground.

The second case 201 may include a second suction portion or inlet 202 through which air may be suctioned in the radial direction. The second suction portion 202 may include one or more through hole formed to pass through at least a portion of the second case 201. A plurality of the second suction portion 202 may be provided.

The plurality of second suction portions 202 may be evenly provided in the circumferential direction along an outer circumferential surface of the second case 201 so that air suction may be performed in any direction relative to the second case 201. That is, air may be suctioned in 360 degree directions relative to a center line that extends in the vertical direction and passes through an inside center of the second case 201.

Accordingly, a suction amount of air may be increased by the second case 201 having a cylindrical shape and the plurality of second suction portions 202 formed along the outer circumferential surface of the second case 201. Flow resistance to suctioned air may be reduced by avoiding a cube shape having an edge portions such as the case of the related are air cleaner. Air which is suctioned in through the second suction portion 202 may flow substantially in the radial direction from the outer circumferential surface of the second case 201.

The air cleaner 10 may include a dividing device or divider 400 which may be provided between the first blowing device 100 and the second blowing device 200. The dividing device 400 may include a dividing plate 430 that separates or blocks air flow generated in the first blowing device 100 and air flow generated in the second blowing device 200. By the dividing plate 430, the first and second blowing devices 100 and 200 may be spaced apart from each other in the vertical direction.

The flow adjusting device 300 may be provided at an upper side of the second blowing device 100. An air flow path of the second blowing device 100 may communicate with an air flow path of the flow adjusting device 300. The air passing through the second blowing device 100 may be discharged through a second discharge portion or outlet 305 to the outside via the air flow path of the flow adjusting device 300. The second discharge portion 305 may be provided on or at an upper end portion of the flow adjusting device 300.

Figure 18:
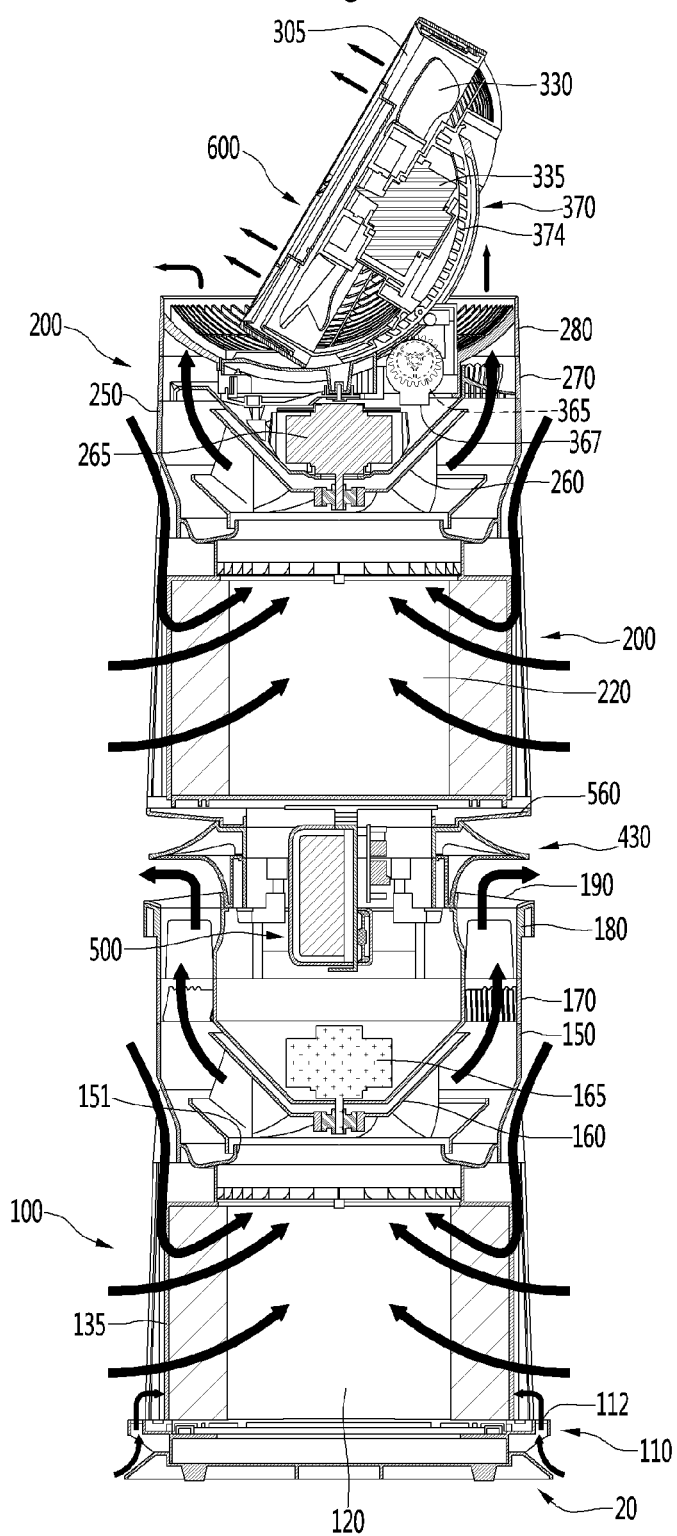

The flow adjusting device 300 may be movable. That is, the flow adjusting device 300 may be movable between a laid-out state (first position), as illustrated in FIG. 1, or an inclined erected state (second position), as illustrated in FIG. 18. In addition, a display device or display 600 that displays operation information of the air cleaner may be provided at an upper portion of the flow adjusting device 300. The display device 600 may be movable together with the flow adjusting device 300.

Figure 2:
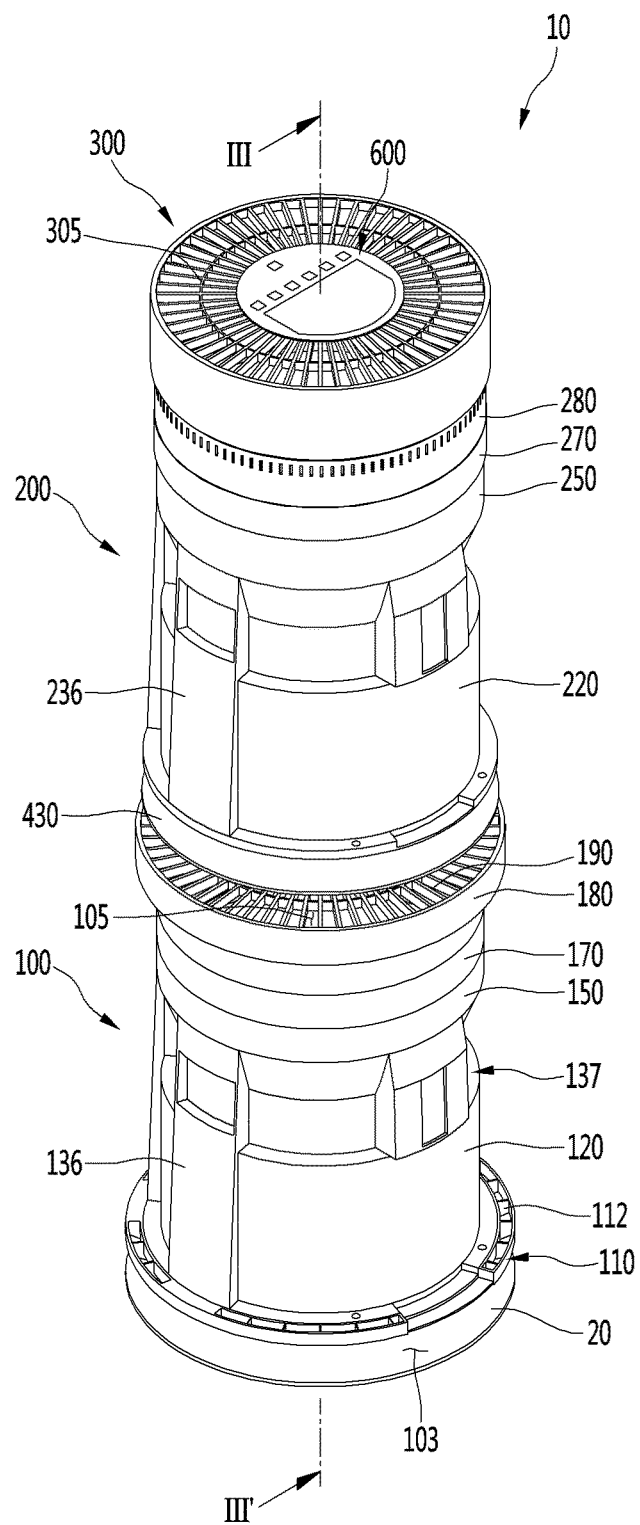
FIG. 2 is a perspective view illustrating an internal configuration of the air cleaner of FIG. 1.
Figure 3:
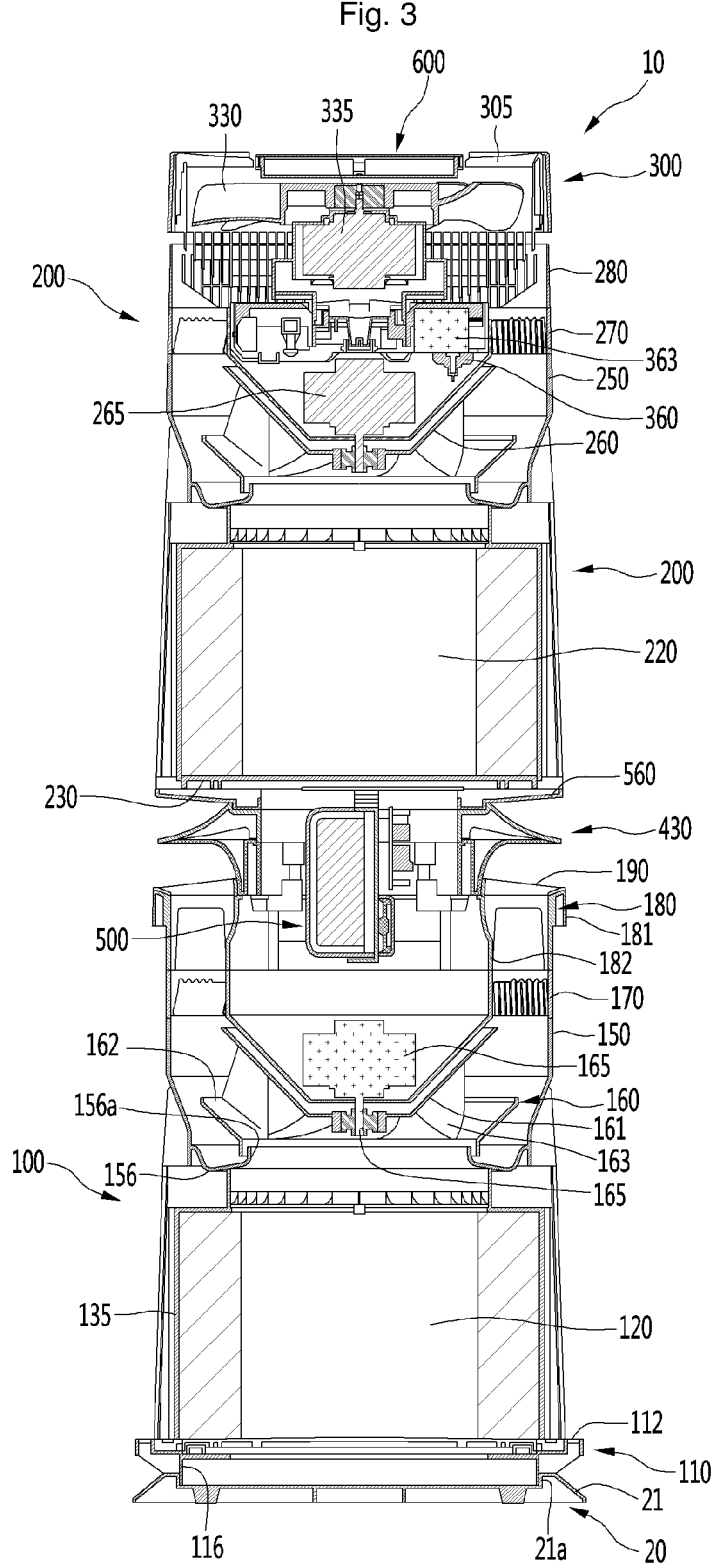
FIG. 3 is a cross-sectional view, taken along line III-III' in FIG. 2.
Figure 4:
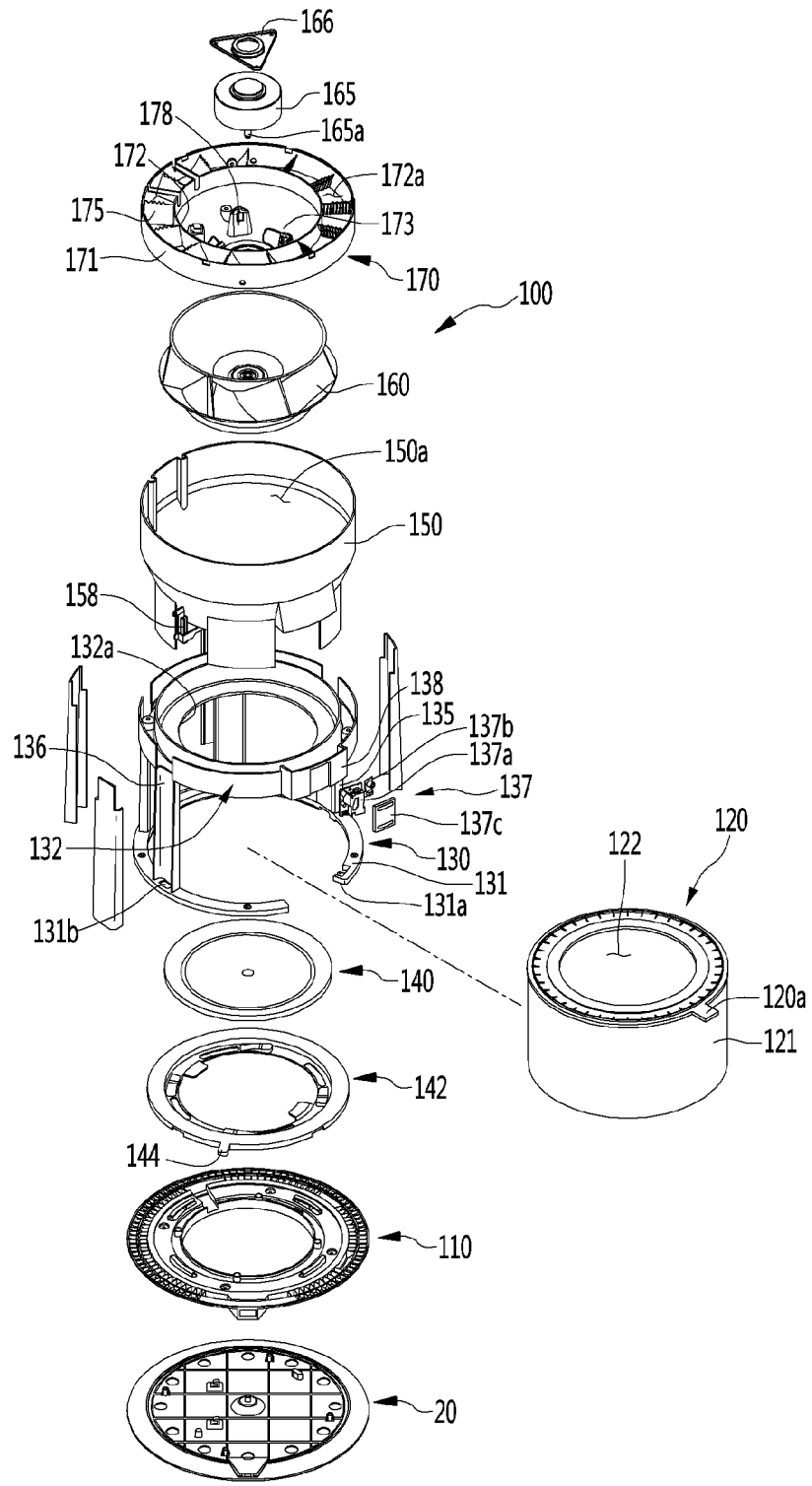
FIG. 4 is an exploded perspective view of a first blowing device according to an embodiment.

FIG. 2 is a perspective view of the air cleaner of FIG. 1. FIG. 3 is a cross-sectional view, taken along line III-III' of FIG. 2. FIG. 4 is an exploded perspective view of the first blowing device according to an embodiment.

Referring to FIGS. 2 and 3, a base 20 and a suction grill 110, which may be disposed or provided on or at an upper side of the base 20 may be included in the first blowing device 100 according to this embodiment. The base 20 may include a base main body 21 having a grill supporting portion or support 21*a*, which may be placed on a ground and support the suction grill 110. The grill supporting portion 21*a* may have a substantially circular shape, and a lower projecting portion or projection 116 of the suction grill 110 may be supported inside of the grill supporting portion 21*a*. The base main body 21 and the suction grill 110 may be spaced apart from each other in a state in which they are coupled to each other. A base suction portion or outlet 103, which may form a suction space for air, may be formed between the base 20 and the suction grill 110.

The first blowing device 100 may include a lever device or lever 142, which may be provided on or at an upper side of the suction grill 110 and which may be operable by a user. The lever device 142 may be rotatable in the circumferential direction. A handle 144 (see FIG. 5) may be provided on or at an outer circumferential surface of the lever main body 143.

A supporting device 140 that supports the first filter 120 may be provided on or at an upper side of the lever device 142. The lever device 142 may support a lower surface of the supporting device 140. The supporting device 140 may be disposed or provided inside of a lower frame 131 to support a lower side of the filter 120, and a plurality of first filter supporting portions or supports 135 may be arrayed along a circumference of the supporting device 140.

The first filter 120 that filters foreign materials in air which is suctioned through the first suction portion 102 or the base suction portion 103 may be provided on or at an upper side of the supporting device 140. The first filter 120 may have a cylindrical shape having an open upper portion, and air may be introduced through an outer circumferential surface of the first filter 120. Impurities, such as fine dust in air, may be filtered in a process of passing through the first filter 120.

The air may be introduced from any direction relative to the first filter 120, due to the first filter 120 having the cylindrical shape. Accordingly, a filtering area of air may be increased.

The first filter 120 may include a filter main body 121 and 125 having a cylindrical filter portion, an inside of which may be empty, and a filter hole 122 formed to be open at an upper end portion or end of the filter main body 121 and 125. The filter main body 121 and 125 may include a first filter portion 121 and a second filter portion 125 (see FIG. 7).

The first filter 120 may further include a filter handle 120*a*, which may be provided at an upper or lower portion of the filter main body 121 and 125. Air may be introduced inside of the filter main body 121 and 125 through the outer circumferential surface of the filter main body 121 and 125, and then discharged from the first filter 120 through the filter hole 122.

The first blowing device 100 may include a first filter frame 130, which may form a mounting space for the first filter 120. That is, the first filter frame 130 may include a lower frame 131, which may form a lower portion of the first filter frame 130 and an upper frame 132, which may form an upper portion of the first filter frame 130.

The lower frame 131 may have a ring shape to surround the lower portion of the first filter 120. In addition, a locking portion or lock 131*b*, to which a locking projection (not shown) of the first case 101 may be coupled, may be formed in the lower frame 131. The locking portion 131*b* may be formed at an outside of the first filter supporting portion 135.

The upper frame 132 may have a ring shape to surround the upper portion of the first filter 120. The upper frame 132 may be spaced apart from the lower frame 131 in the upward direction.

The ring-shaped inside portion of the upper frame 132 may form a frame opening portion or opening 132*a*. The frame opening portion 132*a* may communicate with the filter hole 122 of the first filter 120. That is, the frame opening portion 132*a* may form at least a portion of the flow path of air which passes through the first filter frame 130, and air which is discharged through the filter hole 122 of the first filter 120 may be introduced to a first fan housing 150 through the frame opening portion 132*a*. That is, the first filter 120 may be installed or provided at a suction side of the first fan 160.

The upper portion of the upper frame 132 may support the first fan housing 150. A first fan introducing portion 156 that guides flow of air to the inside of the first fan housing 150 may be formed at a lower portion of the first fan housing 150. A fan introducing hole 156*a*, which may communicate with the frame opening portion 132*a*, may be formed in the first fan introducing portion 156.

That is, the first fan housing 150 may be coupled to the upper side of the upper frame 132, and the fan introducing hole 156*a* and the frame opening portion 132*a* may be aligned in the vertical direction. According to this configuration, air which passes through the frame opening portion 132*a* may be introduced to the inside of the first fan housing 150 through the fan introducing hole 156*a*, and it is possible to prevent the air from leaking to the outside of the first fan housing 150. In addition, it may prevent a finger, for example, of a user, from being put into the first fan housing 150 when the first filter 120 is separated by the grill being provided in the first fan introducing portion 156.

The first filter frame 130 may include a first filter supporting portion or support 135 that extends in the upward direction toward the upper frame 132 from the lower frame 131. By the first filter supporting portion 135, the lower and upper frames 131 and 132 may be spaced apart from each other. A plurality of first filter supporting portions 135 may be provided. The plurality of first filter supporting portions 135 may be arrayed in the circumferential direction to be connected to the lower and upper frames 131 and 132. A mounting space 130*a* (see FIG. 11) of the first filter 120 may be defined by the lower and upper frames 131 and 132 and the plurality of first filter supporting portions 135.

A frame cover 136 may be coupled to an outside of the first filter supporting portion 135. The frame cover 136 may reinforce a supporting force of the first filter supporting portion 135. In addition, a wire space portion or space, in which a wire may be located may be formed between the first filter supporting portion 135 and the frame cover 136. The wire may include an electrical wire, which may connect fan motors 165, 265, and 335, a printed circuit board (PCB) device 500, and a display device or display 600, for example.

A sensor device or sensor 137 may be installed or provided in or on the first filter frame 130. The sensor device 137 may include a dust sensor 137*a* that senses an amount of dust in the air and a gas sensor 137*b* that senses an amount of gas in the air. In addition, the sensor device 137 may further include a sensor cover 137*c* that shields the dust sensor 137*a* and the gas sensor 137*b*.

The dust sensor 137*a* and the gas sensor 137*b* may be supported by the upper frame 132 of the first filter frame 130. A sensor mounting portion or mount 138, in which the sensor device 137 may be installed or provided, may be provided in the upper frame 132. The sensor mounting portion 138 may protrude from an outer circumferential surface of the upper frame 132.

The first blowing device 100 may further include an ionizer 158 that removes or sterilizes smell particles in the air. The ionizer 158 may be coupled to the first fan housing 150 and be capable of acting on the air which flows inside of the first fan housing 150.

The sensor device 137 and the ionizer 158 may also be installed or provided in a second blowing device 200 described hereinafter. For example, the sensor device 137 and the ionizer 158 may be installed or provided in one of the first blowing device 100 or the second blowing device 200.

The first fan 160 may be placed on an upper side of the first fan introducing portion 156, and may be accommodated in a housing space portion 150*a* of the first fan housing 150. For example, the first fan 160 may include a centrifugal fan which introduces air in the axial direction and discharges the air to an upper side in the radial direction.

The first fan 160 may include a hub 161 to which a rotational shaft 165*a* of a first fan motor 165, which may be a centrifugal fan motor, may be coupled, a shroud 162 which may be disposed or provided in a state of being spaced apart from the hub 161, and a plurality of blades 163, which may be disposed or provided between the hub 161 and the shroud 162. The first fan motor 165 may be coupled to the upper side of the first fan 160.

The first blowing device 100 may further include a first air guide device or guide 170 that guides a flow of air being passed through the first fan 160 by being coupled to an upper side of the first fan 160. The first air guide 170 may include an outer wall 171 having a cylindrical shape and an inner wall 172 positioned on or at an inside of the outer wall 171 and having a cylindrical shape. The outer wall 171 may be disposed or provided to surround the inner wall 172. A first air flow path 172*a*, through which air may flow may include circumferential surface of the outer wall 171 and an outer circumferential surface of the inner wall 172.

The first air guide 170 may include a guide rib 175 which may be disposed or provided on or in the first air flow path 172*a*. The guide rib 175 may extend from the outer circumferential surface of the inner wall 172 to the inner circumferential surface of the outer wall 171. A plurality of guide ribs 175 may be disposed or provided spaced apart from each other. The plurality of guide ribs 175 may guide the air introduced to the first air flow path 172*a* of the first air guide 170 via the first fan 160 in the upward direction.

The guide rib 175 may extend at an incline from a lower portion of the outer wall 171 and the inner wall 172 in the upward direction. For example, the guide rib 175 may be rounded, and thus, guide air so that it flows at an incline in the upward direction.

The first air guide 170 may further include a motor accommodating portion 173 that extends from the inner wall 172 to the lower side, and thus, accommodates the first fan motor 165. The motor accommodating portion 173 may have a bowl shape, a diameter of which may be gradually reduced in the downward direction. A shape of the motor accommodating portion 173 may correspond to the shape of the hub 161. The motor accommodating portion 173 may be inserted into the hub 161.

The first fan motor 165 may be supported to or at an upper side of the motor accommodating portion 173. The rotational shaft 165*a* of the first fan motor 165 may extend from the first fan motor 165 in the downward direction and be coupled to the shaft coupling portion 161*a* of the hub 161 through the lower surface portion of the motor accommodating portion 173.

In addition, a motor coupling portion 166 may be provided on or at an upper side of the first fan motor 165. The motor coupling portion 166 may guide the first fan motor 165 to be fixed to the air guide 170.

The first blowing device 100 according to this embodiment may further include a second air guide device or guide 180 which may be coupled to an upper side of the air guide 170 and guide air having passed through the first air guide 170 to the discharging guide 190. The second air guide 180 may include a first guide wall 181, which may have a substantially cylindrical shape, and a second guide wall 182, which may be positioned at an inside of the first guide wall 181 and have a substantially cylindrical shape. The first guide wall 181 may be disposed or provided to surround the second guide wall 182. The PCB device 500, which may control an operation of the air cleaner 10 may be mounted inside of the cylindrical second guide wall 182.

The second blowing device may include a second filter member or filter 220, a second filter frame 230, a second fan housing 250, a second fan 260, and a second fan motor 265. These components may be the same as or similar to the first filter 120, the first filter frame 130, the first fan housing 150, the first fan 160, and the first fan motor 165 of the first blowing device 100, and therefore, repetitive disclosure has been omitted.

In addition, the second blowing device 200 may further include a lever supporting device or support 560 that supports the second filter 220 of the second blowing device 200. The supporting device 140 and the lever device 142, which may be provided in the first blowing device 100, may be provided on or at an upper side of the lever supporting device 560. The description regarding the supporting device 140 and the lever device 142 may be identically to that applied to the second blowing device 200.

The second blowing device 200 may further include a third air guide device or guide 270, which may be coupled to an upper side of the second fan 260 to guide a flow of air which passes through the second fan 260. The third air guide 270 may be the same as or similar to the first air guide 170, and therefore, repetitive disclosure has been omitted.

The second blowing device 200 may include a second discharge guide device or guide 280, which may be disposed or provided on or at an upper side of the third air guide 270 and guide the flow of air passing through the third air guide 270. The air flow control device 300 may be movably provided on or at an upper side of the second discharge guide 280. The air flow control device 300 may include a third fan 330. The third fan 330 may guide air passing through the third air guide 270 to be discharged outside of the air cleaner 10. A third fan motor 335 may be coupled to the third fan 330.

The third fan 330 may include an axial flow fan. That is, the third fan 330 may be operated to allow air introduced in the axial direction by passing through the third air guide 270 to be discharged in the axial direction. The air passing through the third fan 330 may be discharged to the outside through the second discharge portion 305, which may be located on or at an upper side of the third fan 330.

In the air cleaner 10, a discharged blowing amount may be improved, and air may be discharged in various directions as the second discharge portion 305 along with the first discharge portion 105 of the first blowing device 100 may be provided.

The display device 600, which may display operation information of the air cleaner 10, may be provided on or at an upper surface of the air cleaner 10.

The first fan motor 165 and the second fan motor 265 may be disposed or provided in series relative to a longitudinal direction of the air cleaner 10. In addition, the second fan motor 265 and the third fan motor 335 may be disposed or provided in series relative to the longitudinal direction of the air cleaner 10. That is, the first fan 160, the second fan 260, and the third fan 330 may be disposed or provided on a same axial line.

The air flow control device 300 may further include a rotation guide device or guide that guides rotation in the lateral direction of the air flow control device 300 and rotation in the vertical direction of the air flow control device 300. The rotation in the lateral direction may be referred to as a "first direction rotation" and the rotation in the vertical direction may be referred to as a "second direction rotation."

The rotation guide may include a first guide mechanism or guide that guides the first direction rotation of the air flow control device 300 and a second guide mechanism that guides the second direction rotation of the air flow control device 300. The first guide may include a first gear motor 363 that generates a drive force, and a first gear 360, which may be rotatably coupled to the first gear motor 363. For example, the first gear motor 363 may include a step motor, a rotation angle of which may be easily controlled.

The second guide may include a rotation guide member or guide 370 (see FIG. 16) that guides the second direction rotation of the air flow control device 300. The rotation guide 370 may include a rack 374.

The second guide mechanism may include a second gear motor 367 that generates a drive force, and a second gear 365, which may be coupled to the second gear motor 367. For example, the second gear motor 367 may include a step motor. If the second gear motor 367 is driven, the rotation guide 370 may be rotated in the vertical direction by linkage of the second gear 365 and the second rack 374. Accordingly, the air flow control device 300 may perform the second direction rotation according to the movement of the rotation guide 370.

Figure 17:
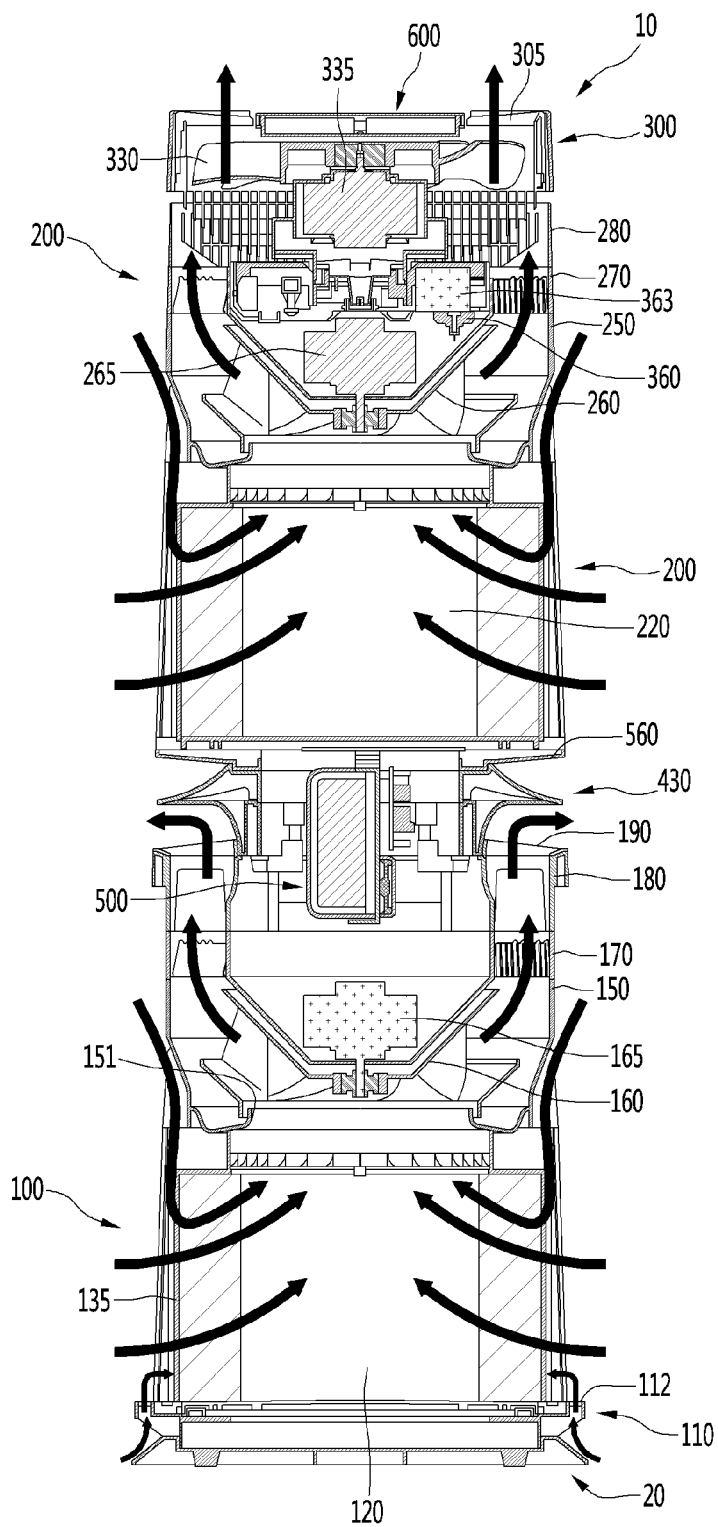

If the air flow control device 300 performs the second direction rotation, the air flow control device 300 may be related to a "second position" at which it protrudes from the upper surface of the air cleaner 10 (see FIG. 18). In contrast, as shown in FIGS. 1 and 17, the position in or at which the air flow control device 300 is laid out may be referred to as a "first position."

Figure 5:
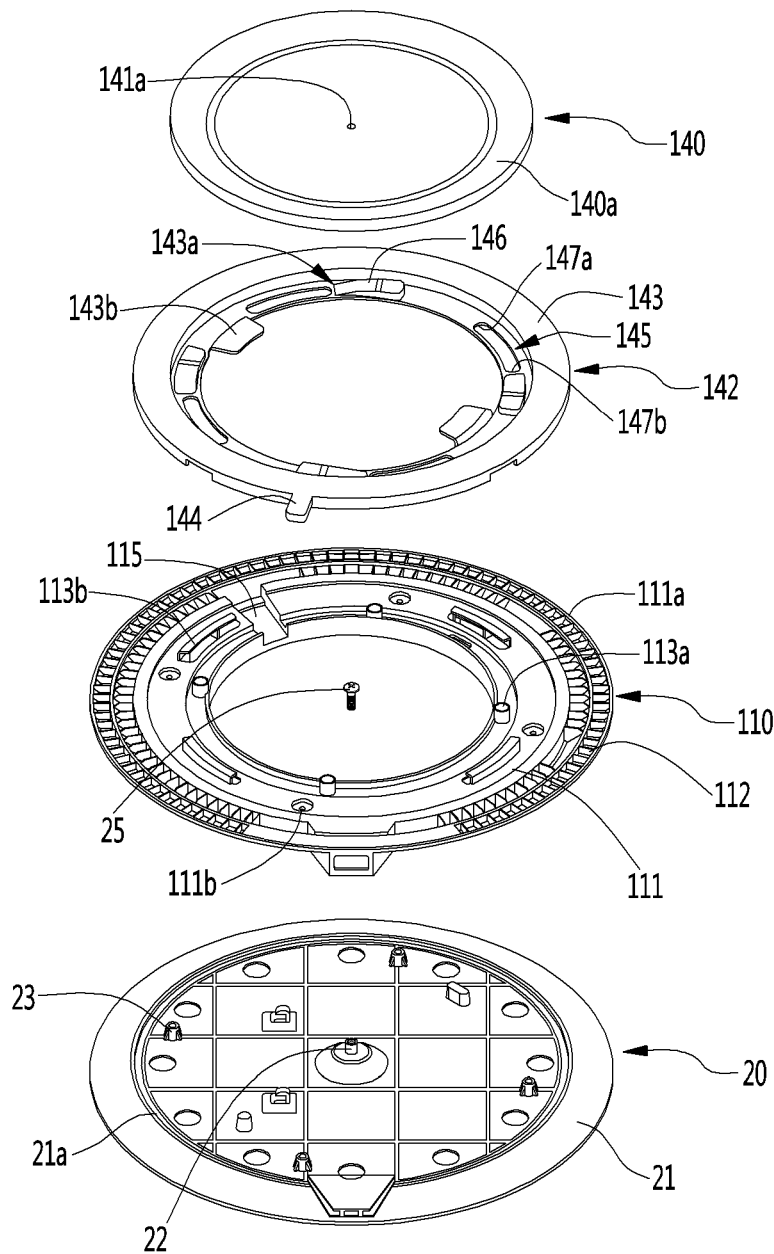
FIG. 5 is an exploded perspective view of components provided at a lower side of a filter according to an embodiment.
Figure 6:
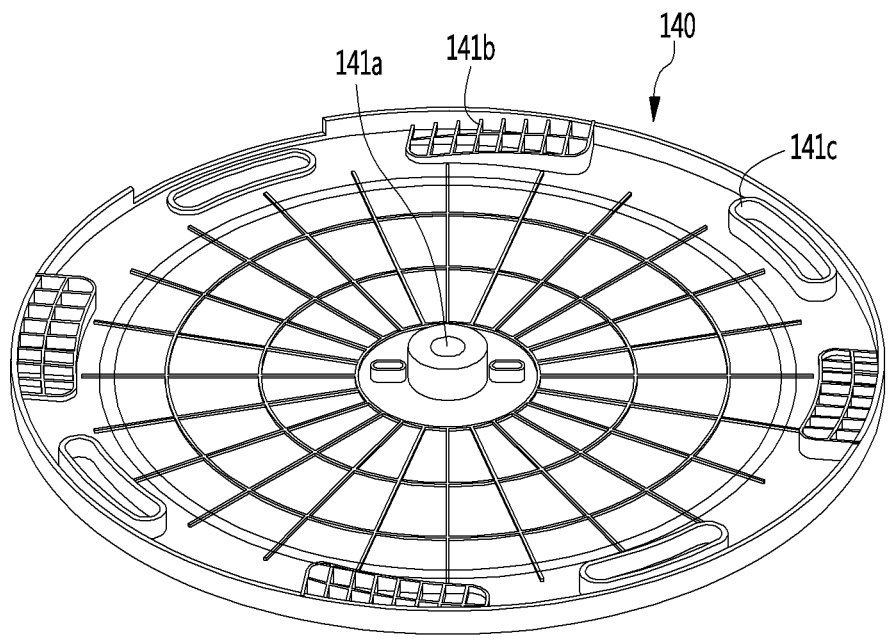
FIG. 6 is a bottom perspective view of a supporting device according to an embodiment.

FIG. 5 is an exploded perspective view of components provided at a lower side of a filter according to an embodiment. FIG. 6 is a bottom perspective view of a supporting device according to an embodiment.

Referring to FIG. 5, the first blowing device 100 according to this embodiment may include the base 20, the suction grill 110, the lever device 142, and the supporting device 140. The base 20 may include the base main body 21, which may have a substantially disk shape. The base main body 21 may include the grill supporting portion 21*a* which supports the lower projecting portion 116 of the suction grill 110. The lower projecting portion 116 may protrude in the downward direction from the ground to be supported by the inside of the grill supporting portion 21*a*.

The base 20 may further include a grill fastening portion 23, which may be fastened to the suction grill 110. The grill fastening portion 23 may be coupled to a base fastening portion 111*b* of the suction grill 110 by a predetermined fastening member. A plurality of grill fastening portions 23 may be provided. For example, as shown in FIG. 5, four grill fastening portions 23 may be provided at a rim portion or rim of the base main body 21.

The base 20 may further include a support coupling portion 22, which may be coupled to the supporting device 140. The support coupling portion 22 may be configured to protrude at a substantially center portion of the base main body 21, and a fastening member 25 may be coupled to the support coupling portion 22. The support coupling portion 22 and the fastening member 25 may support a member insertion portion 141*a* of the supporting device 140, and may guide movement of the supporting device 140.

The supporting device 140 may be movable in the upward or downward direction. The fastening member 25 may serve as a stopper that limits the supporting device 140 so that it is not movable any more in the upward direction in a state in which the supporting device 140 is moved by a set or predetermined distance in the upward direction. In a state in which the supporting device 140 is moved in the upward direction, the first filter 120 may be in a state (first filter position) in which it is coupled to the mounting space 130*a*. On the other hand, in a state in which the supporting device 140 is moved in the downward direction, the first filter 120 may be in a released state (second filter position) in which it is separable from the mounting space 130*a*.

The suction grill 110 may be fixed to the upper side of the base 20. That is, the suction grill 110 may include a grill main body 111, which may have a substantially ring shape and a rim portion or rim 111*a*, which may be provided at the outside of the grill main body 111. The grill suction portion 112, through which air suctioned in through the base suction portion 103 may pass, may be provided in the rim portion 111*a*. The grill suction portion 112 may be formed along a circumference of the rim portion 111*a*.

Air which is suctioned through the grill suction portion 112 may be moved in the upward direction and pass through the first filter 120. The first filter 120 may be provided in a cylindrical shape, and may have a filter surface that filters air. Air which passes through the grill suction portion 112 may be introduced to the inside of the first filter 120 by passing through the outer circumferential surface of the cylindrical first filter 120.

The first case 101 may be supported on or at an upper side of the grill suction portion 112. Thus, air which is suctioned in through the grill suction portion 112 may be added to air which is suctioned in through the first suction portion 102, to pass through the first filter 120.

The suction grill 110 may further include a guide projection 113*a* that guides rotation of the lever device 142. The guide projection 113*a* may protrude in the upward direction from the upper surface of the grill main body 111, and may be inserted into a projection penetrating portion 145 of the lever device 142. In a process of rotation of the lever device 142, the guide projection 113*a* may be moved inside of the projection penetrating portion 145. A plurality of projection penetrating portions 145 may be provided spaced apart from one another in the circumferential direction.

A groove portion or groove 115, which may be depressed in the downward direction from the grill main body 111 to guide a mounting position of the lever device 142, may be formed in the suction grill 110. When the lever device 142 is mounted on or at the upper side of the suction grill 110, the handle 144 of the lever device 142 may be located on or at an upper side of the groove portion 115. At this time, the lever device 142 may be located at a "mounting reference position."

The lever device 142 may include a lever main body 143, which may have a substantially ring shape and be rotatable. The lever device 142 may further include a movement guide portion or guide 143*a* that protrudes in the upward direction from an upper surface of the lever main body 143 to guide movement of the first filter 120 in the upward or downward direction. The movement guide 143*a* may have a shape which gradually protrudes in the circumferential direction from an upper surface of the lever main body 143. That is, the movement guide 143*a* may include an inclined surface 146 that gradually protrudes in the circumferential direction.

A plurality of movement guides 143*a* may be provided spaced apart from one another in the circumferential direction. For example, four movement guides 113 may be provided, as shown in FIG. 5. However, the number of movement guide portions 113 is not limited thereto.

A projection penetrating portion or projection 145, into which the guide projection 113*a* of the suction grill 110 may be inserted, may be formed in the lever device 142. The projection penetrating portion 145 may penetrate at least a portion of the lever main body 143. Also, the projection penetrating portion 145 may be rounded with a predetermined curvature in the circumferential direction, corresponding to a curvature of an outer circumferential surface or inner circumferential surface of the lever main body 143.

In addition, a plurality of projection penetrating portions 145 may be provided spaced apart from one another. The plurality of projection penetrating portions 145 may be arrayed in the circumferential direction of the lever main body 143. The projection penetrating portion 145 may be provided to a number corresponding to that of the guide projections 113*a*. For example, as shown in FIG. 5, four projection penetrating portions 145 may be provided in the circumferential direction.

The guide projection 113*a* may extend to an upper side of the lever main body 143 by passing through the projection penetrating portion from a lower side of the lever main body 143. In a process of rotation of the lever device 142, the guide projection 113*a* may be moved inside of the projection penetrating portion 145.

The projection penetrating portion 145 may include a first end portion or end 147*a* and a second end portion or end 147*b*. The projection penetrating portion 145 may be a through hole that extends from the first end portion 147*a* to the second end portion 147*b*.

When the lever device 142 is located at a "filter released position," the guide projection 113*a* may be located at a position at which it is locked to the first end portion 147*a* of the projection penetrating portion 145. The "filter released position" may be a position for guiding the supporting device 140 to move in the downward direction. The "filter released position" may be a position at which the first filter 120 is capable of being separated from the mounting space 130*a*.

In contrast, when the lever device 142 is located at a "filter mounting position," the guide projection 113*a* may be located at a position at which it is locked to the second end portion 147*b* of the projection penetrating portion 145. The "filter mounting position" may be a position for guiding the supporting device 400 to move in the upward direction. The "filter mounting position" may be a position at which the first filter 120 is coupled to the mounting space 130*a*.

In the process of rotation of the lever device 142, the guide projection 113*a* may be moved from the first end portion 147*a* to the second end portion 147*b*. That is, the guide projection 113*a* may be fixed to the suction grill 110, but may have a relative movement inside of the projection penetrating portion 145 when the lever device 142 is rotated.

The lever device 142 may further include a supporting plate 143*b*, which may extend to the inside in the radial direction from an inner circumferential surface of the lever main body 143. The supporting plate 143*b* may support a lower surface of the supporting device 140. A plurality of supporting plates 143*b* may be provided at both sides of the lever main body 143.

The handle 144, which may be operable by a user to rotate the lever device 142, may be formed on an outer circumferential surface of the lever device 142. A user may rotate the lever device 142 in the clockwise direction or in the counterclockwise direction by manipulating the handle 144.

The supporting device 140 may be movably supported on an upper side of the lever device 142. That is, when the lever device 142 is rotated, the supporting device 140 may interfere with the lever device 142 to perform a movement in the upward or downward direction.

When the supporting device 140 is moved in the upward direction, the supporting device 140 may push the first filter 120 in the upward direction such that the first filter 120 may be supported by the first filter frame 130. In contrast, when the supporting device 140 is moved in the downward direction, the supporting device 140 may pull the first filter 120 in the downward direction such that the first filter 120 is located at a position at which it is separable from the first filter frame 130.

The supporting device 140 may include a supporting main body 140a, which may have a substantially disk shape. The supporting main body 140 may have a filter supporting surface that supports the first filter 120. The supporting device 140 may include a member insertion portion 141a, which may be provided at a substantially center portion of the supporting main body 140a and into which the fastening member 25 may be inserted. The member insertion portion 141a may be a through hole that penetrates in the vertical direction.

The fastening member 25 may extend in the downward direction by being inserted into the member insertion portion 141a at the upper side of the supporting device 140, and may be coupled to the support coupling portion 22 of the base 20. By the fastening member 25, the supporting device 140 may be moved in the upward or downward direction in a state in which its center is fitted with respect to the base 20, the suction grill 110, and the lever device 142 without being shaken in the lateral direction. For example, the fastening member 25 may include a screw.

The supporting device 140 may include a support projecting portion or projection 141b, which may be in contact with the movement guide 143a. The support projecting portion 141b may protrude in the downward direction from the lower surface of the supporting main body 140a, and a plurality of support projecting portions 141b may be provided at positions corresponding to the plurality of movement guides 143a. In addition, a shape of the support projecting portion 141b may correspond to a shape of the movement guide 143a, and include an inclined surface which may gradually protrude in the circumferential surface.

A direction in which the movement guide 143a gradually protrudes and a direction in which the support projecting 141b gradually protrudes may be opposite to each other. For example, if the direction in which the movement guide 143a gradually protrudes is the counterclockwise direction, the direction in which the support projecting portion 141b gradually protrudes may be the clockwise direction. In contrast, if the direction in which the movement guide 143a gradually protrudes is the clockwise direction, the direction in which the support projecting portion 141b gradually protrudes may be the counterclockwise direction.

In a process of rotation of the lever device 142, the movement guide 143a and the support projecting portion 141b may interfere with each other, and the supporting device 140 may perform a movement in the upward or downward direction in this process. That is, if a lower portion of the support projecting portion 141b and an upper portion of the movement guide 143a are in contact with each other when the lever device 142 is located at a position, the supporting device 140 may be moved in the upward direction. In addition, the first filter 120 supported by the supporting device 140 is in a state in which it is coupled to the first blowing device while being moved in the upward direction.

On the other hand, if an upper portion of the support projecting portion 141b and a lower portion of the movement guide 143a are in contact with each other or if the interference between the support projecting portion 141b and the movement guide portion 143a is released when the lever device 142 is located at another position by being rotated, the supporting device 140 may be moved in the downward direction. In addition, the first filter 120 supported by the supporting device 140 may be in a state (released state) in which it is separable from the first blowing device 100.

Figure 7:
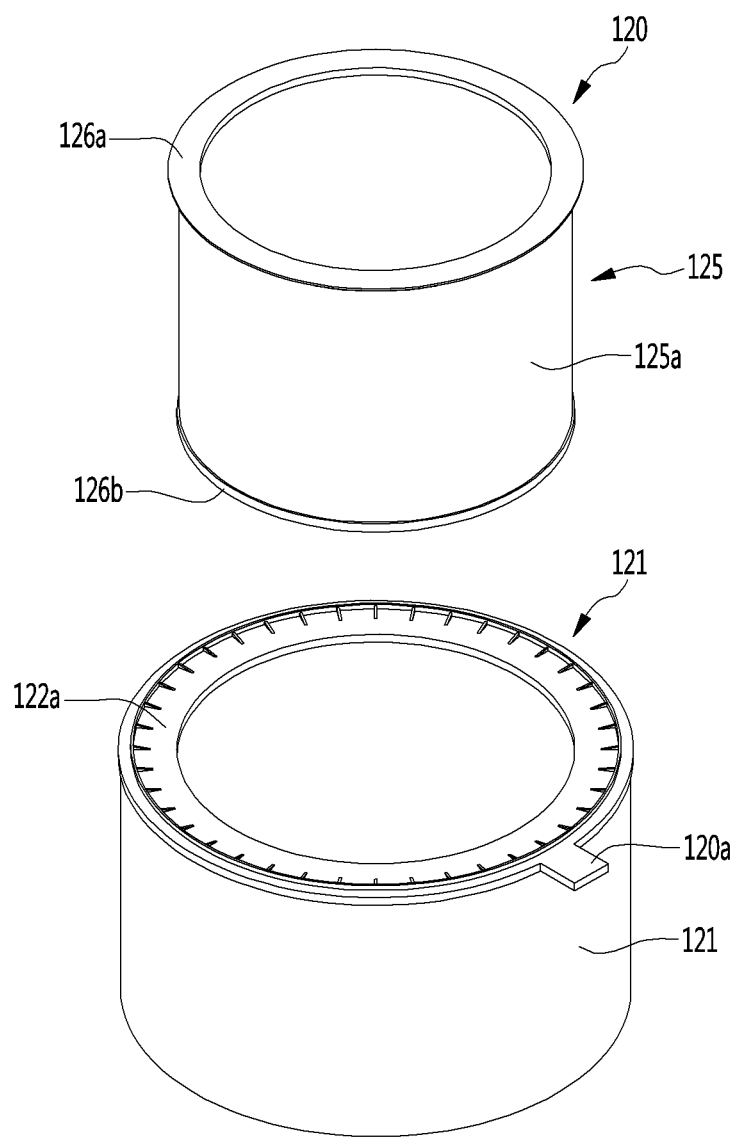
FIG. 7 is an exploded perspective view of a filter according to an embodiment.
Figure 8:
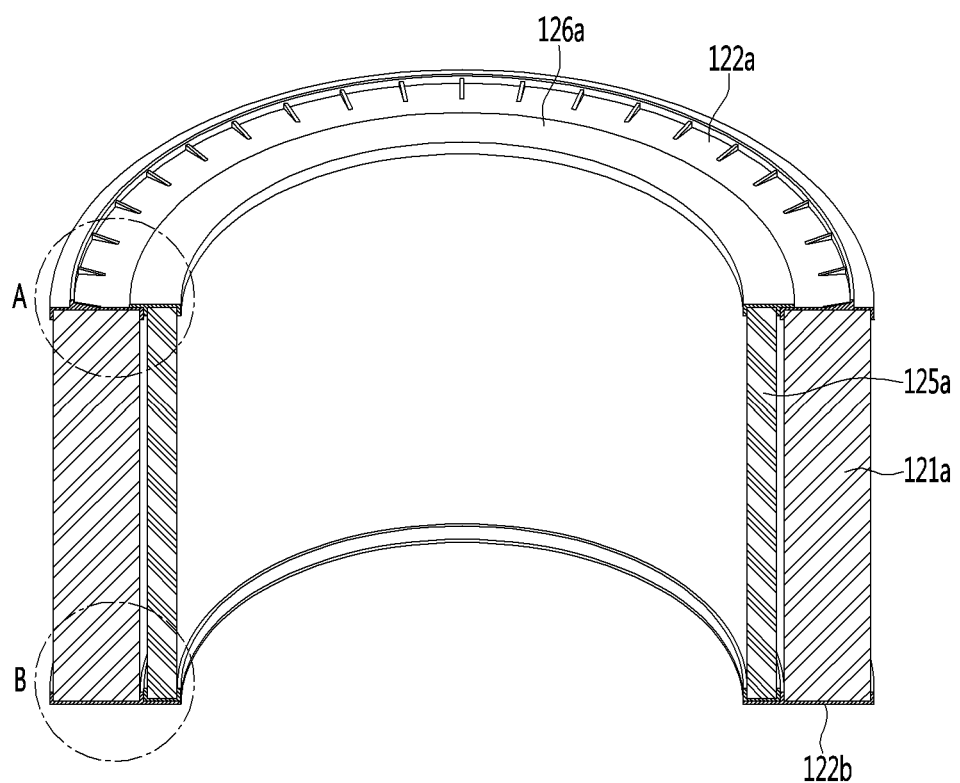
FIG. 8 is a cross-sectional view of a filter according to an embodiment.
Figure 9:
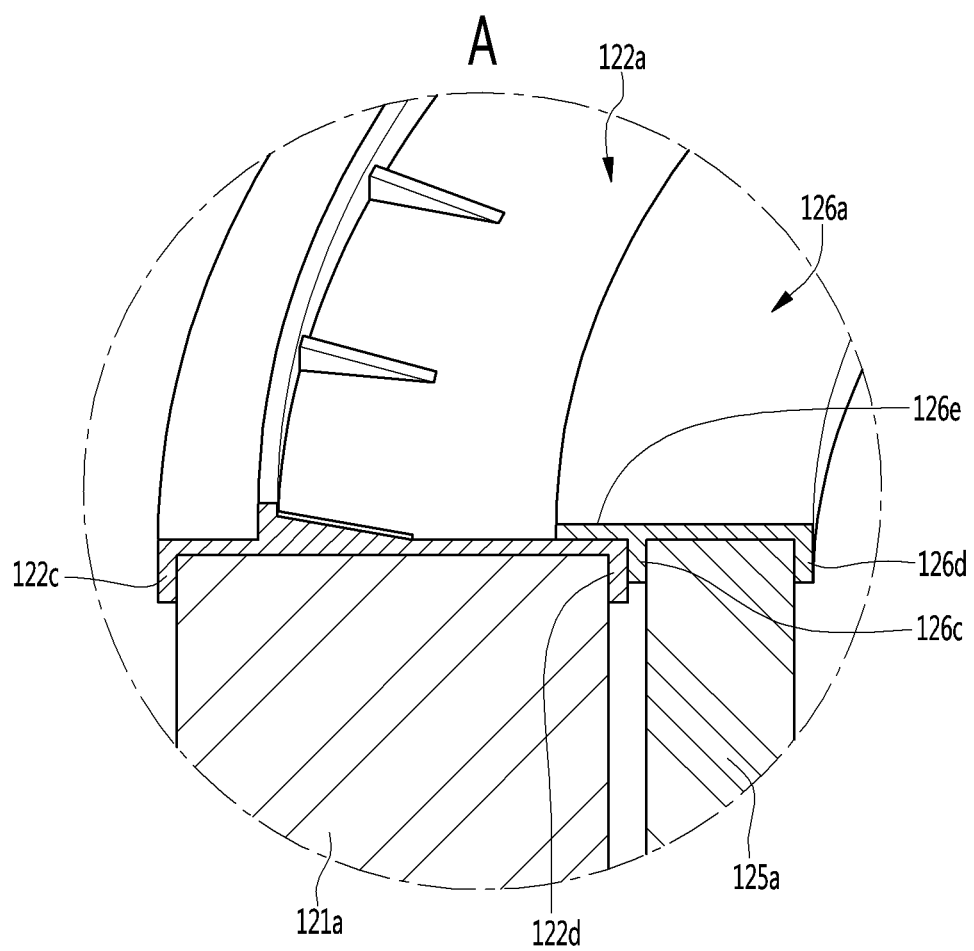
FIG. 9 is an enlarged view of portion "A" of FIG. 8.
Figure 10:
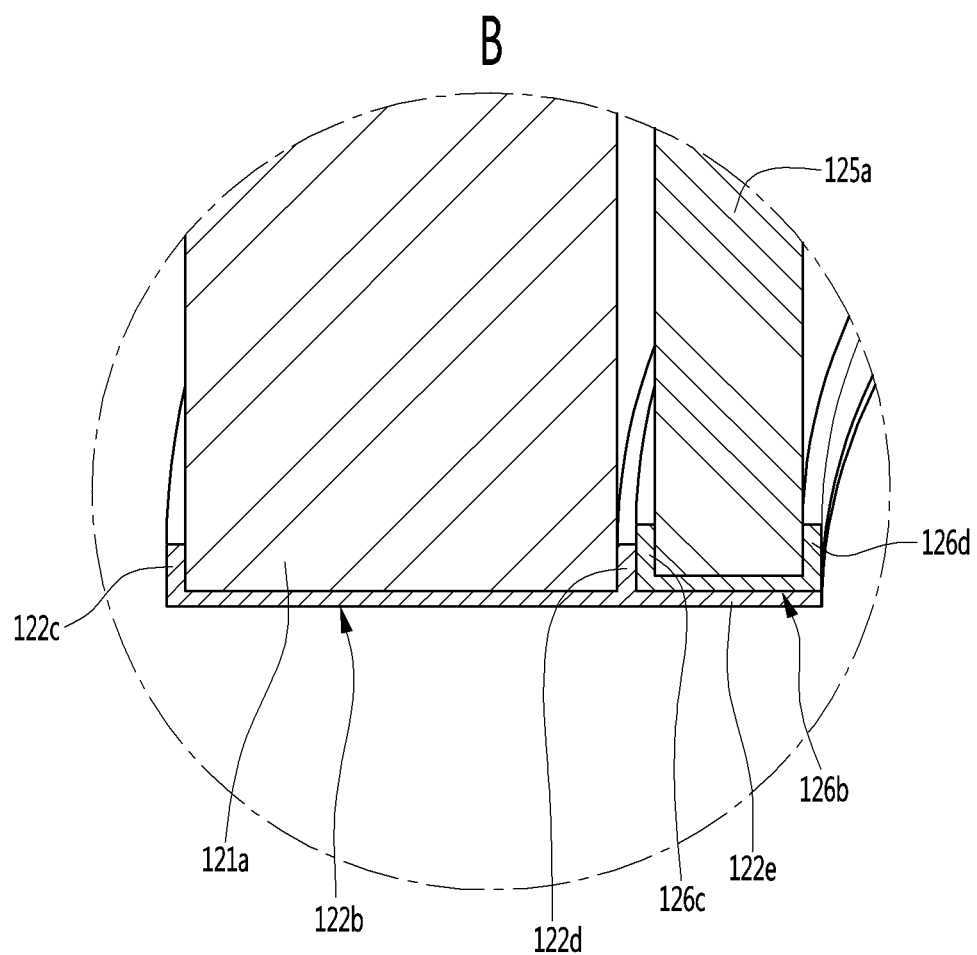
FIG. 10 is an enlarged view of portion "B" of FIG. 8.

FIG. 7 is an exploded perspective view of a filter according to an embodiment. FIG. 8 is a cross-sectional view of a filter according to an embodiment. FIG. 9 is an enlarged view of portion "A" of FIG. 8. FIG. 10 is an enlarged view of portion "B" of FIG. 8.

Referring to FIGS. 7 to 10, the first filter 120 according to this embodiment may include the first filter portion 121 and the second filter portion 125. The second filter portion 125 may be inserted inside of the first filter portion 121.

The first filter portion 121 may be a "foreign material removing filter" that filters microorganism, such as fine dust or viruses in air. For example, the first filter portion 121 may include a HEPA filter. That is, the first filter portion 121 may include a first filter main body 121a, which may have a hollow cylindrical shape, and a fixing frame 122a and 122b that supports the first filter main body 121a. The first filter main body 121a may provide a filter surface that filters foreign materials.

The fixing frame 122a and 122b may include a first fixing frame 122a that supports an upper portion of the first filter main body 121a, and a second fixing frame 122b that supports a lower portion of the first filter main body 121a. The first fixing frame 122a may include a first outer surface supporting portion or support 122c that supports an upper outer circumferential surface of the first filter main body 121a, and a first inner surface supporting portion or support 122d that supports an upper inner circumferential surface of the first filter main body 121a. In other words, the first fixing frame 122a may be coupled to the upper surface, lower outer circumferential surface, and lower inner circumferential surface of the first filter main body 121a by the first outer surface supporting portion 122c and the first inner surface supporting portion 122d.

The second fixing frame 122b may include a first outer surface supporting portion or support 122c that supports the lower outer circumferential surface of the first filter main body 121a, and a first inner surface supporting portion or support 122d that supports the lower inner circumferential surface of the first filter main body 121a. That is, the second fixing frame 122b may be coupled to the lower surface, lower outer circumferential surface, and lower inner circumferential surface of the first filter main body 121a by the first outer surface supporting portion 122c and the first inner surface supporting portion 122d. According to the configuration of the first and second fixing frames 122a and 122b, the first filter portion 121 may be stably maintained in the cylindrical shape thereof.

The first filter portion 121 may further include a filter handle 120a, which may be grasped by a user. The filter handle 120a may be provided on at least one of the first and second fixing frames 122a and 122b. The filter handle 120a may protrude in the radial direction from an outer circumferential surface of the first fixing frame 122a or the second fixing frame 122b.

The second filter portion 125 may be a "deodorizing filter" that filters smell particles in air. That is, the second filter portion 125 may include a second filter main body 125a having a hollow cylindrical shape, and a fixing frame 126a and 126b that supports the second filter main body 125a. The second filter main body 125a may provide a filter surface that filters foreign materials.

The fixing frame 126a and 126b may include a third fixing frame 126a that supports an upper portion of the second filter main body 125a, and a fourth fixing frame 126b that supports a lower portion of the second filter main body 125a. The third fixing frame 126a may include a second outer surface supporting portion or support 126c that supports an upper outer circumferential surface of the second filter main body 125a and a second inner surface supporting portion 126d that supports an upper inner circumferential surface of the second filter main body 125a. That is, the third fixing frame 126a may be coupled to the upper surface, the upper outer circumferential surface, and the upper inner circumferential surface of the second filter main body 125a by the second outer surface supporting portion 126c and the second inner surface supporting portion 126d.

The third fixing frame 126a may further include a locking projection 126e, which may be locked to an upper side of the first fixing frame 122a. If the second filter portion 125 is inserted inside of the first filter portion 121, the locking projection 126e may be supported on an upper surface of the first fixing frame 122a. Accordingly, the second filter portion 125 may be stably supported by the first filter portion 121.

The fourth fixing frame 126b may include a second outer surface supporting portion or support 126c that supports a lower outer circumferential surface of the second filter main body 125a, and a second inner surface supporting portion 126d that supports a lower inner circumferential surface of the second filter main body 125a. That is, the fourth fixing frame 126b may be coupled to the lower surface, lower outer circumferential surface, and lower inner circumferential surface of the second filter main body 125a by the second outer surface supporting portion 126c and the second inner surface supporting portion 126d. According to the configuration of the third and fourth fixing frames 126a and 126b, the second filter portion 125 may stably maintain the cylindrical shape thereof.

The second fixing frame 122b may further include a frame supporting portion or support 126e that supports a lower side of the fourth fixing frame 126b. That is, the second fixing frame 122b may extend to the inside in the radial direction from the lower side of the first filter portion 121 to the lower side of the second filter portion 125, and a portion located on or at a lower side of the second filter portion 125 may form the frame supporting portion 126e. Accordingly, the second filter portion 125 may be stably supported by the first filter portion 121.

Air which flows toward the outer circumferential surface of the first filter 120 through the first suction portion 102 or the base suction portion 103 may be purified while sequentially passing through the first filter portion 121 and the second filter portion 125. The filter hole 122 may be formed at an upper portion of the second filter portion 125. Air which passes through the first filter 120 may be introduced to the first fan 160 while flowing in the upward direction through the filter hole 122.

Figure 11:
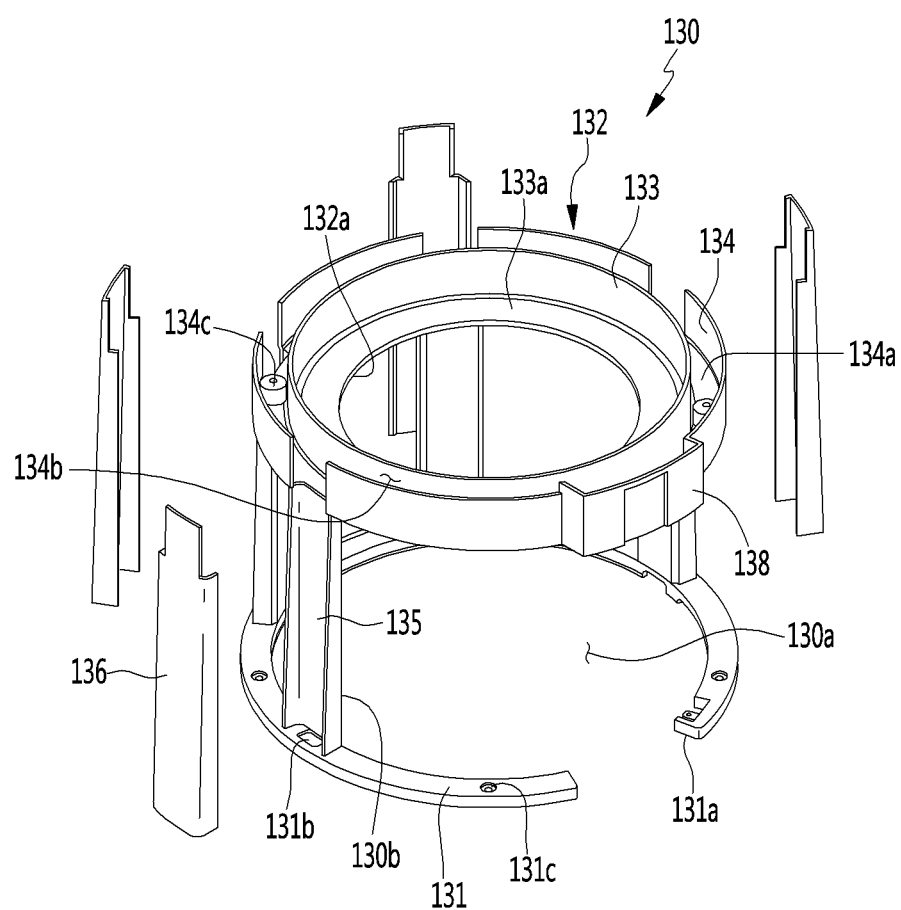
FIG. 11 is a view of a filter frame according to an embodiment.
Figure 12:
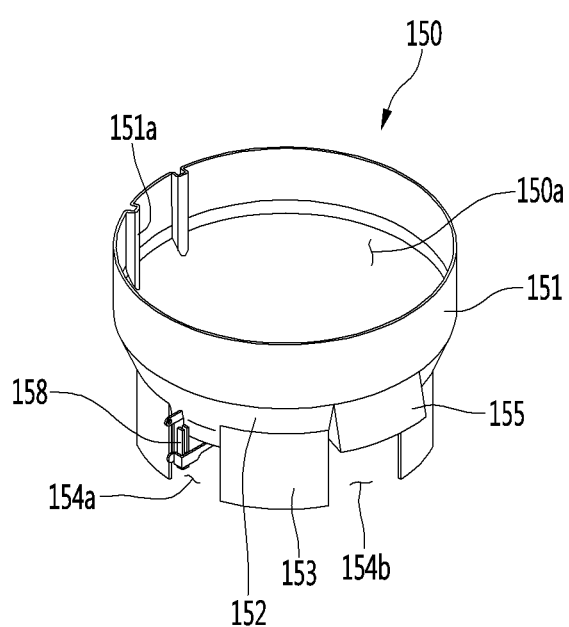
FIG. 12 is a perspective view of a fan housing according to an embodiment.
Figure 13:
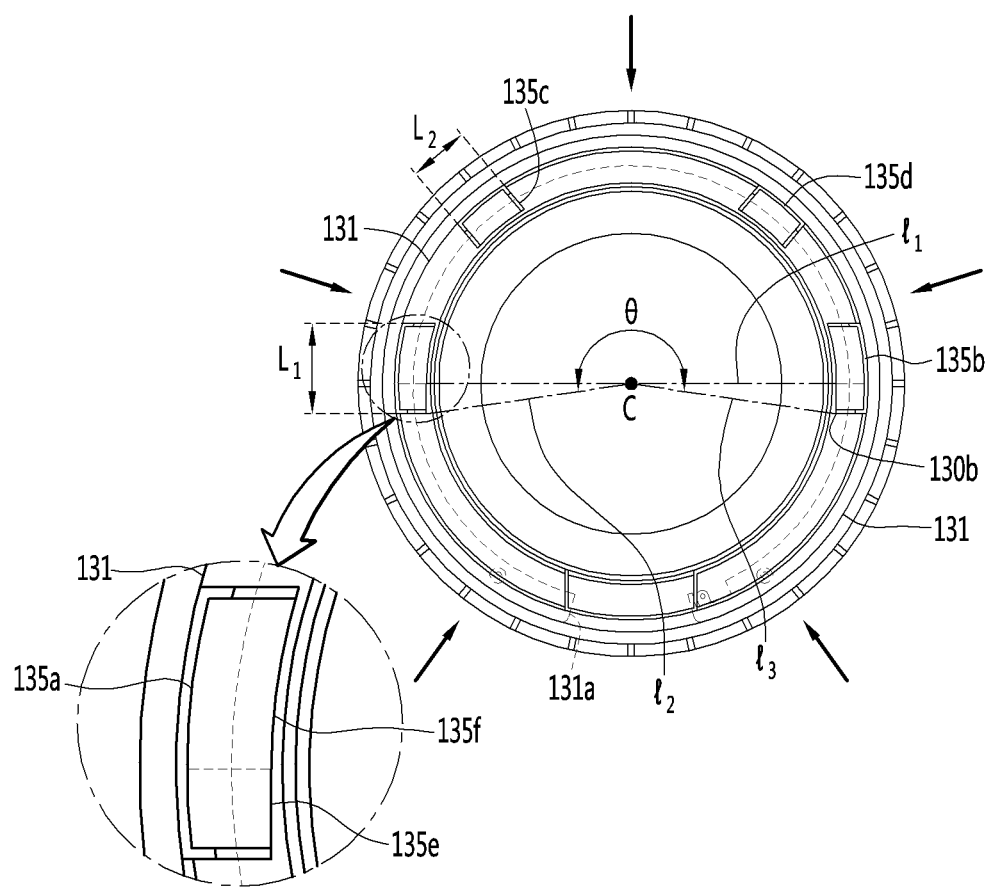
FIG. 13 is a schematic view of the filter frame according to an embodiment.

FIG. 11 is a view of a filter frame according to an embodiment. FIG. 12 is a perspective view of a fan housing according to an embodiment. FIG. 13 is a schematic view of the filter frame according to an embodiment.

Referring to FIGS. 11 to 13, the first filter frame 130 according to this embodiment may include the lower frame 131, which may form a lower portion of the first filter frame 130, the upper frame 132, which may form an upper portion of the first filter frame 130, and the first filter supporting portion or support 135 that extends in the upward direction toward the upper frame 132 from the lower frame 131. A plurality of first filter supporting portions 135 may be provided. The first filter supporting portion 135 may be referred to as a "supporting frame" in that the first filter supporting portion 135 may support an outer surface of the first filter 120.

The mounting space 130a, in which the first filter 120 may be located or provided, may be formed by the lower and upper frames 131 and 132 and the plurality of first filter supporting portions 135. That is, the lower frame 131 may have a ring shape to surround the lower portion of the first filter 120. The lower frame 131 may include a frame cut-out portion or cut-out 131a, which may have a shape formed by cutting out at least a portion of the lower frame 131. The frame cut-out portion 131a may form a space in which the handle 144 of the lever device 142 may be located or provided, and may be formed to have a size corresponding to a rotation path of the handle 144. That is, the frame cut-out portion 131a may provide a space portion or space, in which the handle 144 may be movable.

A frame fastening portion 131c may be formed at the lower frame 131. The frame fastening portion 131c may be coupled to the grill fastening portion 23 of the base 20 and the base fastening portion 111b of the suction grill 110 by a predetermined fastening member.

The upper frame 132 may have a ring shape to surround an upper portion of the first filter 120, and may be spaced apart from the lower frame 131 in the upward direction. In addition, the ring-shape inner portion space of the upper frame 132 may form the frame opening portion 132a. The frame opening portion 132a may communicate with the filter hole 122 of the first filter 120.

The upper frame 132 may include a frame inner wall 133, and a frame outer wall 134 that surrounds the frame inner wall 133. Each of the frame inner wall 133 and the frame outer wall 134 may have a ring shape. In addition, the frame opening portion 132a may be understood as an inner space of the frame inner wall 133.

An inner circumferential surface of the frame outer wall 134 may be spaced apart from an outer circumferential surface of the frame inner wall 133. The upper frame 132 may further include a wall connecting portion 134a that extends to a lower portion of the frame inner wall 133 from a lower portion of the frame outer wall 134.

A housing insertion portion 134b, in which at least a portion of the first fan housing 150 may be located, may be formed in a space defined by the inner circumferential surface of the frame outer wall 134, the outer circumferential surface of the frame inner wall 133, and the wall connecting portion 134a. In addition, a housing coupling portion 134c, which may be coupled to the first fan housing 150, may be provided to or on the wall connecting portion 134a. A plurality of housing coupling portions 134c may be provided at both sides of the wall connecting portion 134a. A predetermined fastening member may be coupled to the housing coupling portion 134c and the frame coupling portion 151a of the first fan housing 150.

The upper frame 132 may further include a housing mounting portion or mount 133a that protrudes from the inner circumferential surface of the frame inner wall 133 to support the first fan housing 150. An inner space of the housing mounting portion 133a may form the frame opening portion 132a.

An upper portion of the upper frame 132 may support the first fan housing 150. The first fan housing 150 may be installed or provided at an outlet side of the first filter 120. That is, the first fan housing 150 may include a housing main body 151, 152, and 153 that forms the housing space portion 150*a*, in which the first fan 160 may be accommodated. The housing main body 151, 152, and 153 may be supported by the first filter frame 130.

The housing main body 151, 152, and 153 may be stepped such that its diameter changes. That is, the housing main body 151, 152, and 153 may include a first main body 151, which may have a set or predetermined first diameter (hereinafter, referred to as a "first set diameter") and a substantially cylindrical shape. The first main body 151 may form an upper portion of the housing main body 151, 152, and 153.

The housing main body 151, 152, and 153 may include a housing cut-out portion or cut-out 154*a* and 154*b*. The housing cut-out portion 154*a* and 154*b* may be formed by cutting out at least a portion of a third main body 153. For example, the housing cut-out portion 154*a* and 154*b* may be cut out by a predetermined height in the upward direction from a lower end portion or end of the third main body 153.

The housing cut-out portion 154*a* and 154*b* may include a first cut-out portion or cut-out 154*a* formed at a position corresponding to the first filter supporting portion 135 to support the first filter supporting portion 135. The first filter supporting portion 135 or the frame cover 136 may be located in the first cut-out portion 154*a*.

The housing cut-out portion 154*a* and 154*b* may include a second cut-out portion or cut-out 154*b* formed at a position corresponding to the sensor mounting portion 138 to support the sensor mounting portion 138. The sensor mounting portion 138 may be located in the second cut-out portion 154*b*. In addition, a sensor supporting portion or support 155, which may be supported by the sensor mounting portion 138, may be disposed or provided on or at an upper side of the second cut-out portion 154*b*. An installation space portion or space, in which the sensor device 137 may be installed or provided, may be defined by the sensor mounting portion 138 and the sensor supporting portion 155.

The third main body 153 may be inserted into the housing insertion portion 134*b*, which may be formed in the upper frame 132. In summary, the third main body 153 may be inserted into the housing insertion portion 134*b*, and the housing cut-out portion 154*a* and 154*b* may support upper portions of the first filter frame 130 and the sensor mounting portion 138, so that the filter frame 130 and the first fan housing 150 may be stably coupled to each other.

The plurality of first filter supporting portions 135 may be arrayed in the circumferential direction along the rim portion of the lower and upper frames 131 and 132, to support the outer circumferential surface of the first filter 120. For example, the plurality of first filter supporting portions 135 may be disposed or provided at a rear portion of the first filter frame 130. In addition, an insertion portion 130*b*, which provides a space into or from which the first filter 120 may be inserted or withdrawn, may be formed at a front portion of the first filter frame 130.

Directions will be defined as follows. A direction in which the first filter 120 is withdrawn may be defined as a "front" of the first filter frame 130, and a direction in which the first filter 120 is inserted may be defined as a "rear" of the first filter frame 130. The frame cut-out portion 131*a* may be formed at a front portion of the lower frame 131, relative to a shape of the lower frame 131.

That is, the insertion portion 130*b* may be formed in a space which is formed at the front of the first filter frame 130 in a space between two first filter supporting portions 135 among the plurality of first filter supporting portions 135. The two first filter supporting portions 135 may include first frames 135*a* and 135*b*. The first frames 135*a* and 135*b* may be disposed or provided opposite to each other.

Second frames 135*c* and 135*d* may be disposed or provided in the circumferential direction in a space which is formed at the rear of the first filter frame 130 in a space between the first frames 135*a* and 135*b*. A plurality of second frames 135*c* and 135*d* may be provided.

FIG. 13 is a schematic view of the filter frame according to an embodiment. That is, FIG. 13 shows the lower frame 131 and the plurality of first filter supporting portions 135 in the first filter frame 130.

The two first frames 135*a* and 135*b* may be disposed or provided opposite to each other, relative to a center C of the lower frame 131. In other words, a center line l1 that passes through the center C may pass through the two first frames 135*a* and 135*b*. An insertion portion 130*b*, from or into which the first filter 120 may be withdrawn or inserted, may be formed in a front space between the two first frames 135*a* and 135*b*, and the second frames 135*c* and 135*d* may be disposed or provided in a rear space.

When considering a supporting force of the first filter frame 130, a supporting force of the front portion of the first filter frame 130, at which the insertion portion 130*b* is formed or provided, may be smaller than a supporting force of the rear portion, at which the second frames 135*c* and 135*d* may be disposed or provided. In this embodiment, the first frames 135*a* and 135*b* may be larger than the second frames 135*c* and 135*d* so as to reinforce the supporting force of the front portion, which is relatively small.

That is, a length L1 in the circumferential direction of the first frames 135*a* and 135*b* may be longer than a length L2 in the circumferential direction of the second frames 135*c* and 135*d*. According to this configuration, the supporting force of the first frames 135*a* and 135*b* may be greater than the supporting force of the second frames 135*c* and 135*d*. Thus, it is possible to reinforce a supporting force, which may be insufficient, as no separate frame is provided at the front portion of the first filter frame 130.

In addition, an angle θ formed by the rear of the center C in two angles made by two extending lines l2 and l3, which respectively extend to front portions of the two first frames 135*a* and 135*b* from the center C, may be equal to or greater than 180 degrees. That is, the front portions of the first frames 135*a* and 135*b* may further extend toward the front, relative to the center C of the lower frame 131, so that it is possible to reinforce the supporting force of the front portion of the first filter frame 130.

Each of the first filter frames 135*a* and 135*b* may include a flat surface or surface portion 135*e* and a curved surface portion or surface 135*f*. The flat surface portion 135*e* may extend toward the rear from the front end portion of the first frames 135*a* and 135*b*, to guide insertion of the first filter 120. In addition, the curved surface portion 135*f* may support the first filter 100 by extending rounded from the flat surface portion 135*e* to the rear. The rounded curvature of the curved surface portion 135*f* may correspond to a curvature of the lower frame 131. That is, as the flat surface portion 135*e* and the curved surface portion 135*f* are provided, the first filter 120 may not interfere with the first frames 135*a* and 135*b* when the first filter 120 is inserted toward the mounting space 130*a*, and the first frames 135*a* and 135*b* may easily support the outer circumferential surface of the first filter 120 when the mounting of the first filter 120 in the mounting space 130*a* is completed.

The first case 101 may be provided at the outside of the lower frame 131. That is, the first case 101 may surround the lower frame 131. If the first fan 160 is driven, air may be suctioned in the radial direction through the first suction portion 102 of the first case 101, and flow into the first filter 120 supported by the first filter frame 130. According to this configuration, air may be suctioned in the circumferential direction of the air cleaner 10, that is, in 360-degree directions, so that a suction capacity of the air cleaner may be increased.

Figure 14:
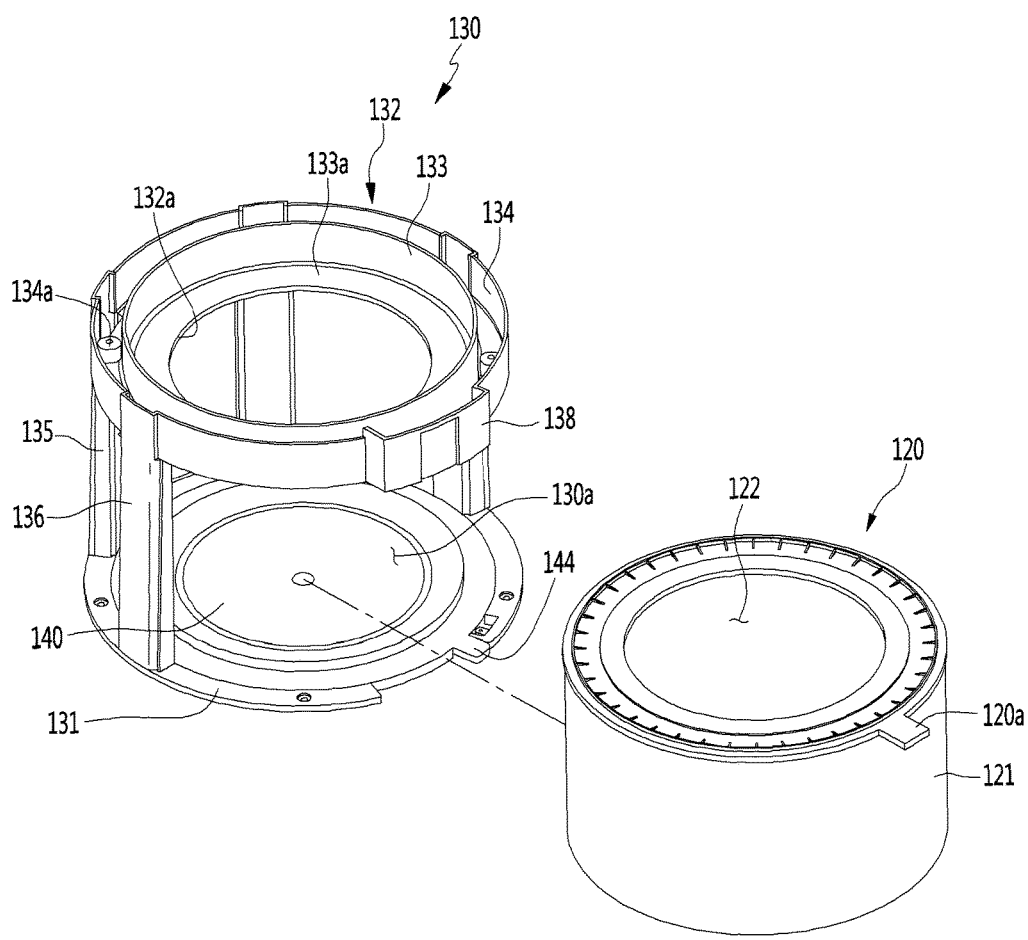
FIGS. 14 and 15 are views illustrating a state in which the filter is assembled and disassembled in a mounting space according to an embodiment.
Figure 15:
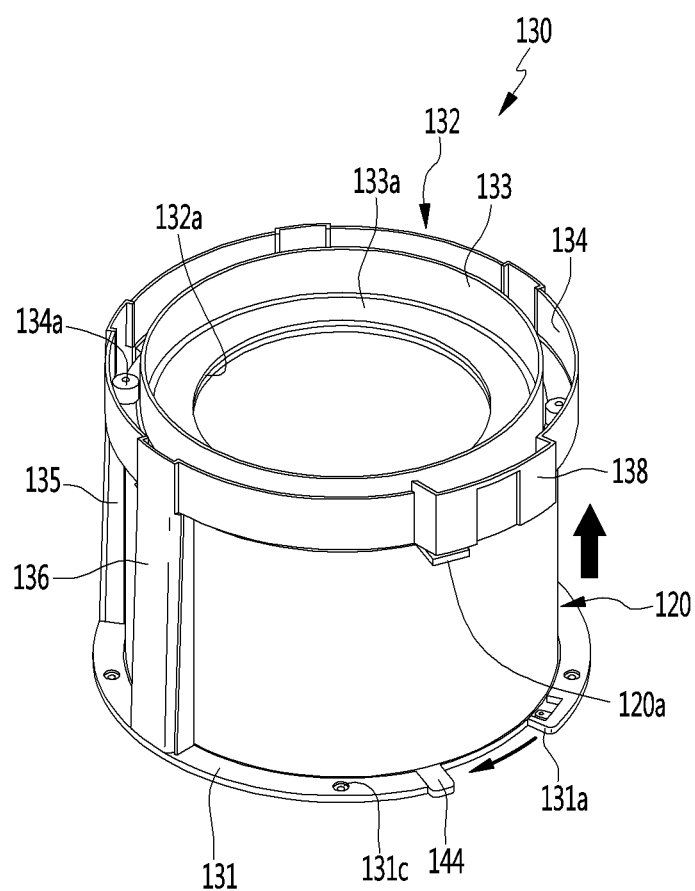

FIGS. 14 and 15 are views illustrating a state in which the filter is assembled and disassembled in a mounting space according to an embodiment. Referring to FIGS. 14 and 15, the first filter 120 may be detachably mounted in the mounting space 130*a* formed in the first filter frame 130 according to an embodiment.

The mounting space 130*a* may be provided in a cylindrical shape, corresponding to the shape of the first filter 120. In a process of mounting of the first filter 120, the first filter 120 may be slidably inserted in the radial direction toward the mounting space 130*a*. In contrast, in a process of separation of the first filter 120, the first filter 120 may be slidably withdrawn in the radial direction from the mounting space 130*a*.

FIG. 14 illustrates a state in which the first filter 120 is separated. In this state, the handle 144 of the lever device 142 may be located at a released position of the first filter 120, for example, one end portion or end of the frame cut-out portion 131*a*. At this time, the position of the handle 144 may be referred to as a "first position" or "released position."

When the handle 144 is located at the first position, the supporting device is in a state in which it is moved in the downward direction. Thus, the mounting space 130*a* forms a space sufficiently large for the first filter 120 to be inserted therein.

In the state of FIG. 14, the first filter 120 may be mounted in the mounting space 130*a* by being moved to the rear through the insertion portion 130*b*. In addition, the supporting device 140 may be moved in the upward direction by rotating the handle 144 in one direction. For example, the handle 144 may be rotated in the clockwise direction, relative to FIGS. 14 and 15.

If the supporting device 140 is moved in the upward direction, the first filter 120 may be adhered closely to the upper portion of the first filter frame 130, that is, the upper frame 132 by being moved in the upward direction. Thus, the first filter 120 may be located at a coupling position.

The supporting device 140 may be moved in the downward direction by rotating the handle 144 in the opposite direction in the state in which the first filter 120 is mounted in the mounting space 130*a*. For example, the handle 144 may be rotated in the counterclockwise direction, relative to FIGS. 14 and 15. If the supporting device 140 is moved in the downward direction, the first filter 120 may be located at a position at which it is separable from the mounting space 130*a*.

Figure 16:
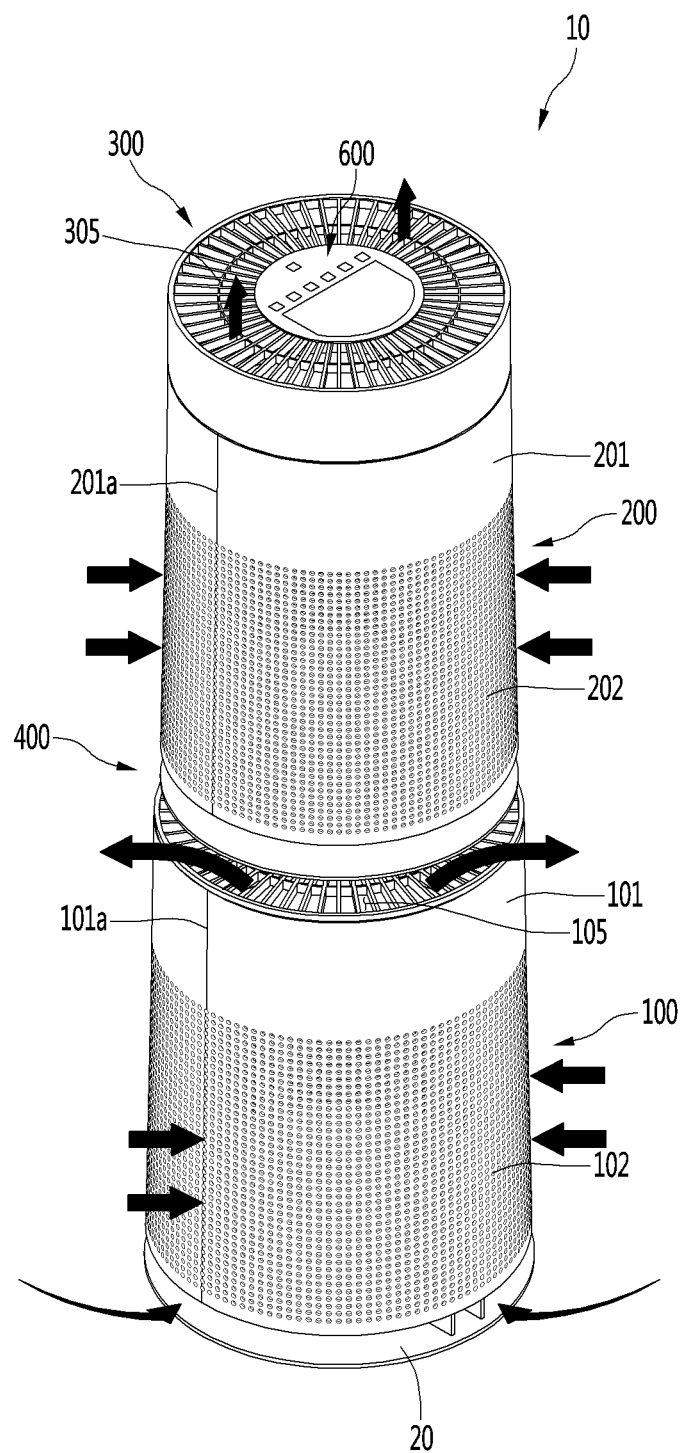
FIGS. 16 to 18 are views illustrating a state in which air flows in the air cleaner of FIG. 1.

FIGS. 16 to 18 are views illustrating a state in which air flows in the air cleaner of FIG. 1.

First, the flow of air according to driving of the first blowing device 100 will be described. If the first fan 160 is driven, indoor air may be suctioned inside portion of the first case 101 through the first suction portion 102 and the base suction portion 103. The suctioned air may pass through the first filter 120, and foreign materials in air may be filtered in this process. In a process in which air passes through the first filter 120, the air may be suctioned in the radial direction of the first filter 120, filtered, and then flows in the upward direction.

That is, air which is suctioned through the lower suction portion 102*a* of the first suction portion 102 may pass through the first filter 120 while flowing into the inside in the radial direction. In addition, air suctioned through the upper suction portion 102*b* may flow in the downward direction along the housing suction flow path 159, and may pass through the first filter 120 by flowing toward the outer circumferential surface of the first filter 120. Air which is suctioned through the base suction portion 103 may pass through the first filter 120 by flowing toward the outer circumferential surface of the first filter 120. In a process in which air suctioned through the first suction portion 102 and the base suction portion 103 passes through the first filter 120, the air may be suctioned in the radial direction of the first filter 120, filtered, and then flow in the upward direction.

The air having passed through the first filter 120 may flow to the upper side in the radial direction while passing through the first fan 160 and stably flow in the upward direction while passing through the first air guide 170 and the second air guide 180. Air passing through the first air guide 170 and the second air guide 180 may pass by the first discharge guide 190 and flow in the upward direction through the first discharge portion 105. Air which is discharged through the first discharge portion 105 may be guided by the dividing plate 430 positioned to the upper side of the first discharge guide 190, and thus, may be discharged outside of the air cleaner 10.

If the second fan 260 is driven, indoor air may be suctioned inside of the second case 201 through the second suction portion 202 and the base suction portion 103. The suctioned air may pass through the second filter 220, and foreign materials in air may be filtered in this process. In a process in which air passes through the second filter 220, the air may be suctioned in the radius direction of the second filter member 220, filtered, and then flow in the upward direction.

That is, air which is suctioned through the lower suction portion 202*a* of the second suction portion 202 may pass through the second filter 220 while flowing into the inside in the radial direction. In addition, air which is suctioned through the upper suction portion 202*b* may flow in the downward direction along the housing suction flow path 259, and pass through the second filter 220 by flowing toward the outer circumferential surface of the second filter 220. In a process in which air passes through the second filter 220, the air may be suctioned in the radial direction of the second filter 220, filtered, and then flow in the upward direction.

Air which passes through the second filter 220 may flow to the upper side in the radial direction while passing through the second fan 160, and stably flow in the upward direction while passing through the third air guide 270 and the second discharge guide 280. Air having passes through the third air guide 270 and the second discharge guide 280 may be discharged through the second discharge portion 305 via the air flow control device 300.

At this time, if the air flow control device 300 is in the first position in which the air flow control device 300 is laid out, as shown in FIG. 17, air which is discharged from the air flow control device 300 may flow in the upward direction. On the other hand, if the air flow control device 300 is in the second position in which the air flow control device 300 is inclined, as shown in FIG. 18, air which is discharged from the air flow control device 300 may flow toward the front upper side. By the air flow control device 300, an amount of air which is discharged from the air cleaner 10 may be increased, and purified air may be supplied to a position a far distant from the air cleaner 10.

Figure 19:
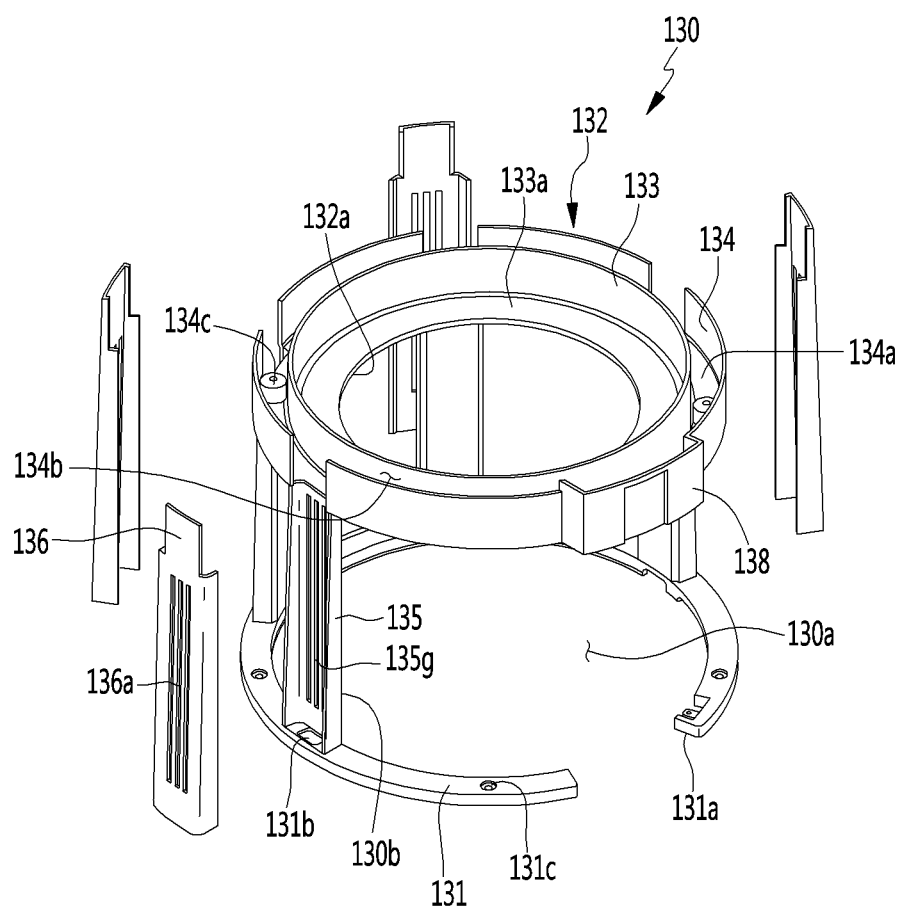
FIG. 19 is a view of a filter frame according to another embodiment.

FIG. 19 is a view of a filter frame according to another embodiment. Referring to FIG. 19, the first filter frame 130 according to this embodiment may include a flow guide portion or guide 135g and 136a that guides flow of air such that air which is suctioned through the first suction portion 102 or the base suction portion 103 may be easily introduced to the first filter 120.

The flow guide 135g and 136a may include a first flow guide portion or guide 135g, which may be provided to or on the first filter supporting portion 135. The first flow guide 135g may be formed at each of the first frames 135a and 135b and the second frames 135c and 135d. In addition, the flow guide 135g and 136a may further include a second flow guide portion or guide 136a provided to or on the first supporting cover 136.

The flow guide 135g and 136a may include a slit through which air may pass. As the flow guide 135g and 136a is provided, air may be introduced to the first filter 120 by passing through the first supporting portion cover 136 and the first filter supporting portion 135. That is, it is possible to prevent a phenomenon that the first supporting portion cover 136 and the first filter supporting portion 135 act as a resistance against flow of air.

According to embodiments disclosed herein, as a suction portion may be formed along an outer circumferential surface of a cylindrical case, and air may be suctioned in a radial direction through a suction portion or inlet, a suction capacity may be improved, and a structural resistance of the case may not be generated in an air suction process. In particular, a plurality of apertures may be included on the suction portion and a suction flow path, which may be directed to the inside of the air cleaner may be formed in 360-degree directions relative to the air cleaner, as the plurality of apertures may be formed evenly over an entire outer circumferential surface of the case. Finally, a suction area of air may be increased and air around a person in a room may be sufficiently suctioned where the person in the room sitting down or standing up.

A filter member of filter may be stably supported by a filter frame, and is capable of being conveniently mounted in a mounting space formed in or at an inside portion of the filter frame. In particular, the filter member may be coupled to the mounting space by being moved in the radial direction and may be separated from the mounting space by being moved in the radial direction from the mounting space, so that a user's convenience for filter attachment and detachment may be enhanced.

As the filter member may be provided in a cylindrical shape, air is may be introduced to the inside portion of the filter member in all directions from the outside of the filter member, so that a suction area may be increased. Accordingly, an air cleaning ability of a filter may be improved. In addition, the filter frame may include a lower frame, which may be provided at a lower portion of the filter member, an upper frame which may be provided at an upper portion of the filter member, and a supporting frame that extends toward the upper frame from the lower frame, so that a mounting space of the filter member may be provided, thereby improving spatial utilization of the air cleaner.

As a plurality of supporting frames may be provided, the upper frame and the lower frame may be stably supported. Further, it is possible to stably support components of the air cleaner, which may be provided or at an upper side of the filter frame. The plurality of supporting frames may include two lower frames and an upper frame which may be disposed at a rear portion in a space between the two lower frames, and an insertion portion into or from which the filter member may be inserted or withdrawn may be formed at a front portion in the space between the two lower frames. Accordingly, the filter member may be easily attached and detached, and a fan, which may be provided on or at an upper side of the filter member, may be stably supported.

Further, as a length (or width) in a circumferential direction of the lower frame may be greater than a length (or width) in the circumferential direction of the upper frame, a supporting force at the front portion in the space between the two lower frames may be reinforced. In addition, a lever device may include a supporting device or support and a handle may be provided on or at a lower side of the filter member, and a movement to a mounting position or released position of the filter member may be easily performed by manipulating the handle.

The supporting frame may include a flow guide portion or guide (slit) which may guide air suctioned in through the suction portion or inlet of the case to the filter member, so that air may be smoothly flow. In addition, the first case or the second case may be stably supported by the filter frame, and a suction portion or inlet formed in each of the first and second cases may be located to come relatively close to the filter member. Finally, it is possible to reduce a flow loss of air which flows into the filter member through the suction portion.

A blowing capacity of the air cleaner may be improved as a plurality of blowing devices may be provided. The air which flows in the radial direction through a centrifugal fan may be easily guided toward a discharge portion in the upward direction, as the centrifugal fan for increasing the blowing capacity of the air cleaner and the air guide which may be disposed on or at an outlet side of the centrifugal fan may be provided.

A phenomena that interference between the air flows may be prevented as the air flows which are independent from each other are generated through the first blowing device and the second blowing device. Accordingly, a air flowing capacity may be improved. Blowing amount may be increased since as the turbo fan which suctions air in an axial direction and then discharges air in the radial direction may be included in the blowing fan.

Embodiments disclosed herein provide an air cleaner which is capable improving a suction capacity of air which is suctioned into the air cleaner. Embodiments disclosed herein also provide an air cleaner which improves a position of a suction inlet formed in a case, thereby increasing a flow amount of air which is suctioned through the suction inlet.

Embodiments disclosed herein provide an air cleaner which enables air suctioned in through the suction inlet to easily flow into a filter member or filter by improving a shape of a fan housing that accommodates a fan of the air cleaner therein. In particular, embodiments disclosed herein provide an air cleaner which enables air flow toward the filter member to be smoothly performed by improving the shape of the fan housing such that a size of an air flow path disposed or provided toward the filter member from the suction portion.

Embodiments further provide an air cleaner which enables a case to be easily separated and enables a user to easily access inner components of the air cleaner by improving a structure of the case. Embodiments also provide an air cleaner a blowing capacity of which may be increased.

Embodiments provide an air cleaner which improves a purification capacity of a filter and in which replacement of the filter may be easily performed. In particular, embodiments provide an air cleaner that includes a filter member or filter which may be easily detachable from a inside portion of a cylindrical case. Embodiments also provide an air cleaner in which a filter member may be capable of being stably supported.

Embodiments additionally provide an air cleaner in which a fan housing disposed or provided at an outlet portion of the filter may be stably supported.

Embodiments disclosed herein an air cleaner that may include a cylindrical case including a suction portion or inlet to suction air in a radial direction; a filter member or filter configured to be detachably provided in the case and having a cylindrical shape; and a filter frame configured to support the filter member. The filter frame may include a lower frame provided at a lower part or portion of the filter member; an upper frame provided at a upper part or portion the filter member; and a plurality of supporting frames that extends toward the upper frame from the lower frame. An entry portion may be formed between the plurality of supporting frames, the entry portion being configured to receive the filter member. The plurality of supporting frames may be arrayed in a circumferential direction.

The plurality of supporting frames may include two first frames, and a second frame disposed or provided in a space between the two first frames. The space may include a front portion and a rear portion. The entry portion may form the front portion of the space. The second frame may be disposed or provided in the rear portion of the space. A length of the first frame in the circumferential direction may be longer than that of the second frame.

The first or second frame may include an air flow guide portion or guide which guides the air suctioned through the suction portion to the filter member. The air flow guide portion may include a slit.

The two first frames and the second frame may be disposed to support an outer circumferential surface of the filter member. The first frame may include a flat surface portion or surface configured to guide a mounting of the filter member, and a curved surface portion or surface configured to extend toward the second frame from the flat surface in a rounded shape and to support the filter member. The second frame may be provided in plural.

The air cleaner may further include a frame cover coupled with an exterior of the supporting frame, and a wire space portion or space formed between the supporting frame and the frame cover and in which a wire may be disposed or provided. The air cleaner may further include a supporting member or support disposed or provided inside of the lower frame to support the lower side of the filter member. The plurality of supporting frames may be arrayed along a perimeter of the supporting member.

The air cleaner may further include a handle installed or provided in or at a lower side of the supporting member, the handle being manipulated to move the filter member in the upward or downward direction. The filter member may move in the upward direction to be mounted in a mounting space inside of the filter frame when the handle rotates in one or a first direction. The filter member may move in the downward direction to be in a location where the filter member is detachable from the mounting space when the handle rotates in the other or a second direction.

Embodiments disclosed herein further provide an air cleaner that may include a case including a suction portion or inlet to suck air in a radial direction; a filter member or filter detachably provided in the case; a fan disposed or provided in an outlet side of the filter member; a lower frame provided at a lower part or portion of the filter member; an upper frame provided at an upper part or portion of the filter member; and a supporting frame that extends toward the upper frame from the lower frame. The lower frame, the upper frame and the supporting frame may form a mounting space of the filter member. The filter member may move toward the mounting space in the radial direction to be mounted therein.

The case may have a cylindrical shape, and the suction portion may be formed in an outer circumference surface of the case to guide an air suctioned in the radial direction. The supporting frame may include a plurality of first frames. An entry portion of the mounting space may be formed in or at a front portion of the space between the plurality of first frames.

The supporting frame may include a second frame which may be disposed or provided in a rear portion of the space between the plurality of first frames.

The air cleaner may further include a fan housing which receives the fan. The upper frame may support the fan housing.

The details of one or more embodiments are set forth in the accompanying drawings and the description. Other features will be apparent from the description and drawings, and from the claims.

Any reference in this specification to "one embodiment," "an embodiment," "example embodiment," etc., means that a particular feature, structure, or characteristic described in connection with the embodiment is included in at least one embodiment. The appearances of such phrases in various places in the specification are not necessarily all referring to the same embodiment. Further, when a particular feature, structure, or characteristic is described in connection with any embodiment, it is submitted that it is within the purview of one skilled in the art to effect such feature, structure, or characteristic in connection with other ones of the embodiments.

Although embodiments have been described with reference to a number of illustrative embodiments thereof, it should be understood that numerous other modifications and embodiments can be devised by those skilled in the art that will fall within the spirit and scope of the principles of this disclosure. More particularly, various variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:
1. An air cleaner, comprising:
a cylindrical case including an inlet through which air is suctioned in a radial direction into the cylindrical case;
a filter configured to be detachably provided in the case and having a cylindrical shape; and
a filter frame configured to support the filter, wherein the filter frame includes:
a lower frame provided at a lower portion of the filter;
an upper frame provided at an upper portion of the filter; and
a plurality of supporting frames that extends toward the upper frame from the lower frame, wherein an entry portion for the suctioned air is formed between the plurality of support frames, the entry portion being configured to receive the filter.
2. The air cleaner of claim 1, wherein the plurality of supporting frames is arrayed in a circumferential direction.

3. The air cleaner of claim 2, wherein the plurality of supporting frames includes:
   two first frames; and
   at least one second frame provided in a space between the two first frames.

4. The air cleaner of claim 3, wherein the space includes a front portion and a rear portion, and the entry portion forms a front portion of the space.

5. The air cleaner of claim 4, wherein the second frame is provided in the rear portion of the space.

6. The air cleaner of claim 3, wherein a length of the first frame in a circumferential direction is longer than a length of the second frame.

7. The air cleaner of claim 3, wherein the first frame or the second frame may include an air flow guide that guides the air suctioned through the suction inlet to the filter.

8. The air cleaner of claim 7, wherein the air flow guide includes a slit.

9. The air cleaner of claim 3, wherein the two first frames and the second frame support an outer circumferential surface of the filter.

10. The air cleaner of claim 3, wherein the first frame includes:
   a flat surface configured to guide a mounting of the filter; and
   a curved surface configured to extend toward the second frame from the flat surface in a rounded shape and to support the filter.

11. The air cleaner of claim 3, wherein the at least one second frame includes a plurality of second frames.

12. The air cleaner of claim 1, further including:
   a frame cover coupled with an exterior of the plurality of supporting frames; and
   a wire space formed between the plurality of supporting frames and the frame cover and configured to receive therein a wire.

13. The air cleaner of claim 1, further including a support provided inside of the lower frame to support a lower side of the filter, wherein the plurality of supporting frames is arrayed along a perimeter of the support.

14. The air cleaner of claim 13, further including a handle at a lower side of the support, the handle being configured to be manipulated to move the filter in an upward or downward direction.

15. The air cleaner of claim 14, wherein the filter moves in the upward direction to be mounted in a mounting space inside of the filter frame when the handle rotates in a first direction, wherein the filter moves in the downward direction to be at a location at which the filter is detachable from the mounting space when the handle rotates in a second direction.

16. An air cleaner, including:
   a case including a suction inlet to suction air in a radial direction;
   a filter detachably provided in the case;
   a fan provided at an outlet side of the filter;
   a lower frame provided at a lower portion of the filter;
   an upper frame provided at an upper portion of the filter; and
   a plurality of supporting frames that extends toward the upper frame from the lower frame and arrayed in a circumferential direction, wherein the lower frame, the upper frame, and the plurality of supporting frames form a mounting space for the filter, wherein the filter moves toward the mounting space in the radial direction to be mounted therein, and wherein the case surrounds the plurality of supporting frames.

17. The air cleaner of claim 16, wherein the case has a cylindrical shape, and where the suction inlet is formed in an outer circumference surface of the case to guide air suctioned in the radial direction.

18. The air cleaner of claim 16, wherein the plurality of supporting frames includes a plurality of first frames, and wherein an entry portion of the mounting space is formed at a front portion of the space between the plurality of first frames.

19. The air cleaner of claim 18, wherein the plurality of supporting frames includes a second frame which is provided at a rear portion of the space between the plurality of first frames.

20. The air cleaner of claim 19, further including a fan housing that receives the fan, wherein the upper frame supports the fan housing.

* * * * *